(12) United States Patent
Braeckmans et al.

(10) Patent No.: US 10,746,730 B2
(45) Date of Patent: Aug. 18, 2020

(54) METHOD AND SYSTEM FOR CHARACTERIZING EXTRACELLULAR VESICLES

(71) Applicant: UNIVERSITEIT GENT, Ghent (BE)

(72) Inventors: Kevin Braeckmans, Lokeren (BE); Stephan Stremersch, Ghent (BE); Andre Skirtach, Gentbrugge (BE); Stefaan De Smedt, Mariakerke (BE); Koen Raemdonck, Ghent (BE); Joseph Demeester, Ghent (BE); Juan Fraire, Ghent (BE)

(73) Assignee: UNIVERSITEIT GENT, Ghent (BE)

( * ) Notice: Subject to any disclaimer, the term of this patent is extended or adjusted under 35 U.S.C. 154(b) by 33 days.

(21) Appl. No.: 16/063,380

(22) PCT Filed: Dec. 18, 2016

(86) PCT No.: PCT/EP2016/081628
§ 371 (c)(1),
(2) Date: Jun. 18, 2018

(87) PCT Pub. No.: WO2017/103245
PCT Pub. Date: Jun. 22, 2017

(65) Prior Publication Data
US 2018/0372730 A1    Dec. 27, 2018

(30) Foreign Application Priority Data
Dec. 18, 2015    (EP) .................................... 15201241

(51) Int. Cl.
*G01J 3/44*    (2006.01)
*G01N 33/543*    (2006.01)
*G01N 21/65*    (2006.01)
*G01N 33/50*    (2006.01)
*G01N 33/92*    (2006.01)

(52) U.S. Cl.
CPC ....... *G01N 33/5432* (2013.01); *G01N 21/658* (2013.01); *G01N 33/5076* (2013.01);
(Continued)

(58) Field of Classification Search
CPC ............... G01N 33/5432; G01N 33/92; G01N 33/54346; G01N 33/5076;
(Continued)

(56) References Cited

U.S. PATENT DOCUMENTS

| 2009/0097022 | A1* | 4/2009 | Shen ................ B29D 11/00365 356/301 |
| 2011/0294691 | A1 | 12/2011 | Erickson et al. |
| 2018/0085320 | A1* | 3/2018 | Zhang .................... A61K 45/06 |
| 2018/0116956 | A1* | 5/2018 | Ciccocioppo ........... A61P 37/00 |

OTHER PUBLICATIONS

Lee et al., "3D Plasmonic Nanobowl Platform for the Study of Exosomes in Solution," Nanoscale, vol. 7, 2015, pp. 9290-9297.
(Continued)

*Primary Examiner* — Abdullahi Nur
(74) *Attorney, Agent, or Firm* — Workman Nydegger

(57) ABSTRACT

A method for characterizing extracellular vesicles at an individual level is described. It comprises obtaining a sample comprising extracellular vesicles to be characterized and functionalizing the extracellular vesicles with plasmonic nanoparticles or a plasmonic coating. The method further comprises irradiating the individual extracellular vesicles with a laser beam and detecting a surface enhanced Raman spectroscopy signal from said individual extracellular vesicle.

15 Claims, 14 Drawing Sheets

(52) U.S. Cl.
CPC . G01N 33/54346 (2013.01); G01N 33/54373 (2013.01); G01N 33/92 (2013.01); *G01N 21/65* (2013.01); *G01N 2800/7028* (2013.01)

(58) Field of Classification Search
CPC .......... G01N 33/54373; G01N 21/658; G01N 2800/7028; G01N 21/65; G01J 3/44; G01J 3/02
See application file for complete search history.

(56) References Cited

OTHER PUBLICATIONS

Smith et al., "Single Exosome Study Reveals Subpopulations Distributed Among Cell Lines with Variability Related to Membrane Content," Journal of Extracellular Vesicles, vol. 4, 2015, 16 Pages.

Kerr et al., "Raman Spectroscopy and SERS Analysis of Ovarian Tumour Derived Exosomes (TEXs): a Preliminary Study," Biophotonics: Photonic Solutions for Better Health Care IV, vol. 9129, 2014, 10 Pages.

Montecalvo et al., "Exosomes as a Short-Range Mechanism to Spread Alloantigen between Dendritic Cells During T Cell Allorecognition," The Journal of Immunology, Apr. 25, 2016, 12 Pages.

Alhasan et al., "Exosome Encased Spherical Nucleic Acid Gold Nanoparticle Conjugates as Potent MicroRNA Regulation Agents," Small, vol. 10, No. 1, Jan. 15, 2014, pp. 186-192.

Van Lehn et al., "Lipid Tail Protrusions Mediate the Insertion of Nanoparticles into Model Cell Membranes," Nature Communications, vol. 5, No. 4482, 2014, 12 Pages.

European Office Communication from EP Application No. 15201241.5, dated Jun. 1, 2016.

International Search Report and Written Opinion from PCT Application No. PCT/EP2016/081628, dated Mar. 20, 2017.

* cited by examiner

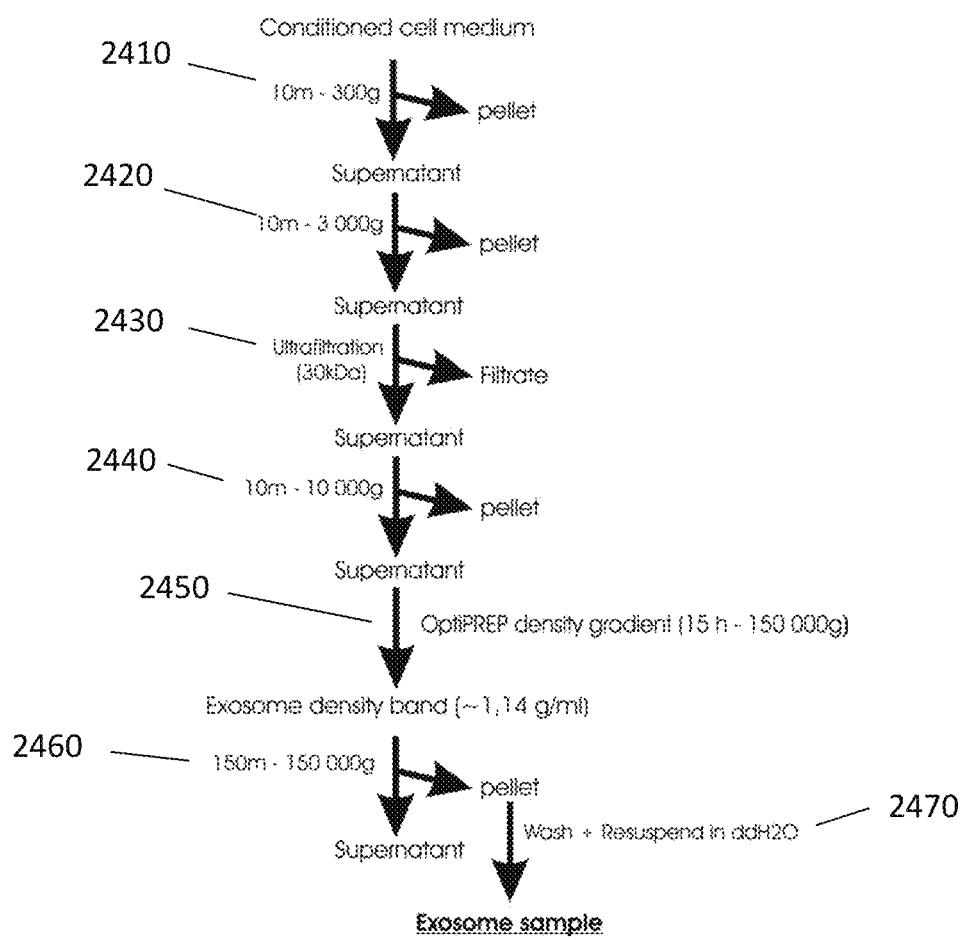
FIG. 24
FIG. 25A
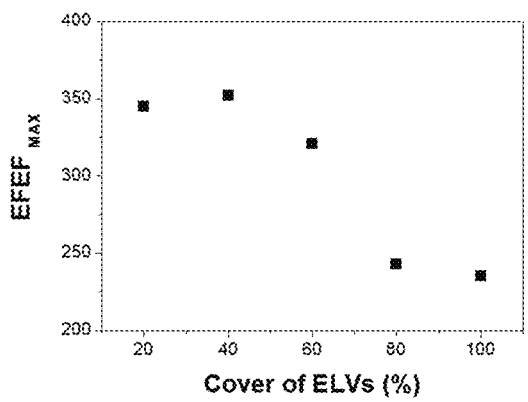
FIG. 25B
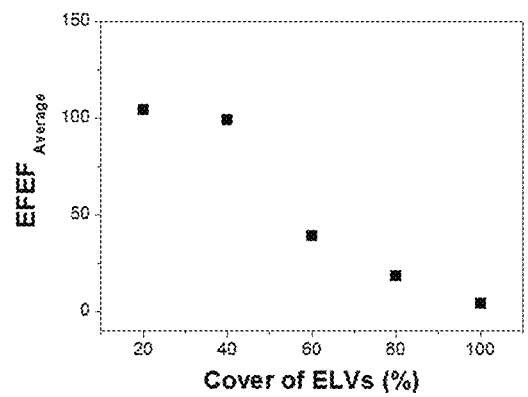

FIG. 26A
FIG. 26B
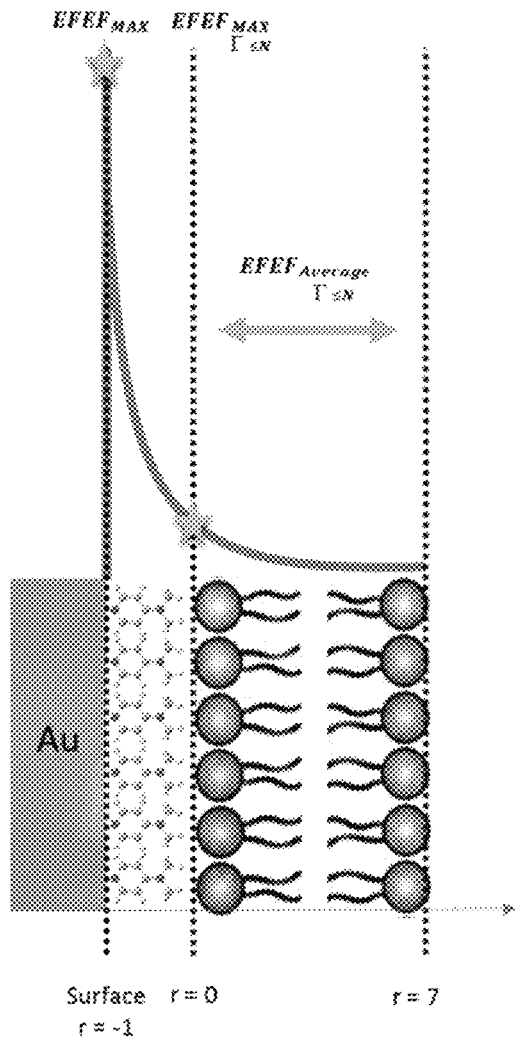
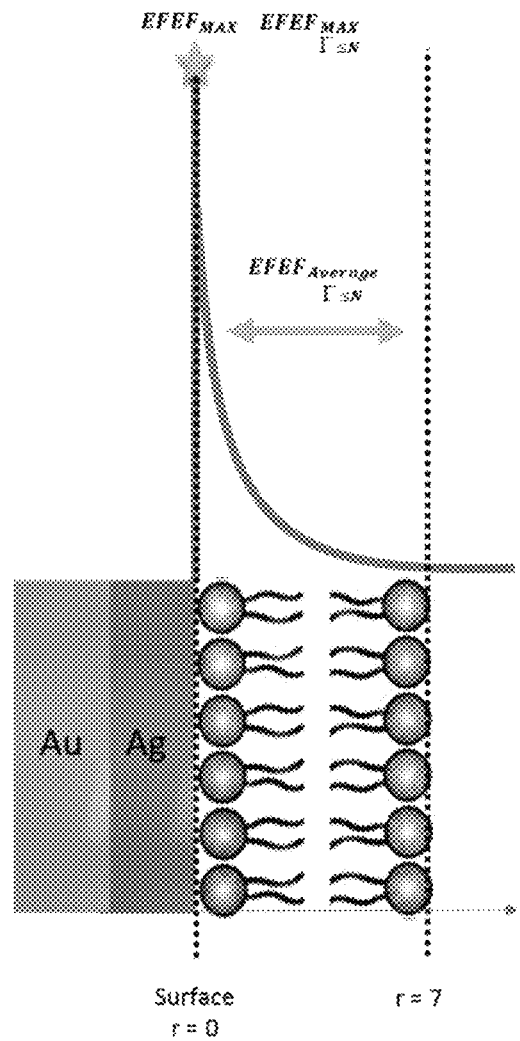

METHOD AND SYSTEM FOR CHARACTERIZING EXTRACELLULAR VESICLES

FIELD OF THE INVENTION

The invention relates to the field of biomarkers for evaluating disease detection and progression. More specifically it relates to methods and systems for characterizing extracellular vesicles.

BACKGROUND OF THE INVENTION

Extracellular vesicles are membrane enclosed vesicles released by all cells. Based on the biogenesis pathway different types of vesicles can be identified: (1) Exosomes are formed by inward budding of late endosomes forming multivesicular bodies (MVB) which then fuse with the limiting membrane of the cell concomitantly releasing the exosomes. (2) Shedding vesicles are formed by outward budding of the limiting cell membrane followed by fission. Finally, (3) when a cell is dying via apoptosis, the cell is desintegrating and divides its cellular content in different membrane enclosed vesicles termed apoptotic bodies. These mechanisms allow the cell to discard waste material and were more recently also associated with intercellular communication. Their primary constituents are lipids, proteins and nucleic acids. They are composed of a protein-lipid bilayer encapsulating an aqueous core comprising nucleic acids and soluble proteins. Currently, extracellular vesicles that are released in bodily fluids (e.g. blood, urine, saliva) receive a lot of attention as possible biomarkers for disease detection and progression, e.g. tumor growth and metastasis. Substantial efforts go into developing techniques suitable for extracellular vesicle identification. Identifying the origin of extracellular vesicles is typically done using biomolecular characterization techniques to determine the protein, nucleic acid and lipid content. One interesting alternative approach is the use of Raman spectroscopy as the Raman spectrum of extracellular vesicles may reveal their composition—and therefore their origin—in a label free manner.

To maximize the impact of current cancer treatments it is advantageous to detect carcinogenic cells in an early stage. To this end, the discovery of sufficiently sensitive and specific biomarkers is of foremost importance. Recently, circulating extracellular vesicles, especially exosomes, have emerged as a potential new class of biomarkers for early detection and treatment monitoring in cancer and other diseases.

Extracellular vesicles are of interest for diagnostic and prognostic applications as they contain molecules derived directly from the parent cell. In addition, they are fairly easily accessible as they are found in various body fluids (e.g. blood, salvia, urine, breast milk, ascites . . . ).

Currently, most extracellular vesicles based diagnostic approaches focus on one specific molecular component as a biomarker for the presence of diseased cells by elaborate genomic, proteomic, metabolomic and lipidomic studies. Examples are elevated levels of miR-21 in exosomes of hepatocellular cancer patients and the presence of EGFRvIII mutant proteins on extracellular vesicles derived from a specific glioblastoma subtype. Despite the fact that these techniques provide detailed molecular information, they require complicated and time-consuming protocols. Additionally, these analyses are performed on the overall extracellular vesicle population level which makes it less likely to find low abundant subpopulations. Considering that most cells secrete extracellular vesicles as part of their normal function, it is to be expected that the amount of vesicles derived from diseased cells is comparatively low. Accordingly, the detection of altered levels of low abundant components in a bulk analysis is quite challenging. Furthermore, it is becoming apparent that one cell type may release multiple subtypes of extracellular vesicles due to which bulk analysis is prone to missing specific subtypes or subtype ratios of vesicles.

SUMMARY OF THE INVENTION

It is an object of embodiments of the present invention to provide a method and a system for characterizing, e.g. improving the characterization, of extracellular vesicles.

The above objective is accomplished by a method and device according to the present invention.

It is an advantage of embodiments of the present invention that systems and methods are provided that are capable of identifying individual extracellular vesicles. The latter may be advantageous since it may be expected that the amount of 'diseased cell'-derived vesicles is low.

The present invention relates to a method for characterizing extracellular vesicles at an individual level, the method comprising obtaining a sample comprising extracellular vesicles to be characterized, functionalizing the extracellular vesicles with plasmonic material, and irradiating the functionalized individual extracellular vesicles with a laser beam and detecting a surface enhanced Raman spectroscopy signal from said individual extracellular vesicle. Functionalizing the extracellular vesicles with plasmonic material thereby comprises providing a coating of plasmonic material on the extracellular vesicles or providing at least one plasmonic nanoparticle to the membrane or in a phospholipid bilayer or in the core/lumen of the extracellular vesicles, Irradiating may for example be performed using an external radiation source, e.g. through a radiation window, or may for example be performed using an integrated radiation source, e.g. in a lab-on-chip system.

Providing at least one plasmonic nanoparticle may comprise providing a plurality of nanoparticles. Providing the at least one plasmonic nanoparticle may comprise attaching a plurality of plasmonic nanoparticles to the surface of the extracellular vesicles and/or may comprise introducing plasmonic nanomaterial on the inside of the exosomes (in the lumen) or may comprise plasmonic nanomaterial being introduced in the phospholipid bilayer.

In advantageous embodiments, the plasmonic material may be plasmonic nanoparticles. In other embodiments, the plasmonic material may be a coating of plasmonic material.

It was surprisingly found that characterisation of extracellular vesicles could be performed at individual level. It is an advantage of embodiments of the present invention that the individual extracellular vesicles are functionalized such that the functionalized individual extracellular vesicles are colloidal stable. This is an advantage over, for example systems wherein exosome agglomerates are produced, such that study of single exosome articles is not possible. This advantageously overcomes the problems of the low abundancy of extracellular vesicles stemming from pathological cells, if one wants to detect pathologies in an early state, which results in a low degree of detectability if characterization techniques are used that operate at population level. By being capable of determining the origin of extracellular vesicles at the individual level, i.e. at a particle by particle base, the detectability of pathologies based on characterization of extracellular vesicles can be drastically improved.

According to embodiments of the present invention, the vesicles may be functionalized such that these are physicochemically repelling each other. The latter may advantageously assist in avoiding clustering such that the functionalized vesicles can be studied independently. The physicochemical repelling may be based for example on charge or may be based on steric effects.

It is an advantage of embodiments of the present invention that analysis of individual extracellular vesicles allows to identify rare types in polydisperse extracellular vesicles samples.

It is an advantage of embodiments of the present invention that individual enhanced Raman spectroscopy signals from an individual extracellular vesicle can be detected. This enables for example individual exosome fingerprinting allowing identification of single exosomes in complex mixtures. This as compared to prior art systems wherein exosomes from different origin appear in a mixture hampering the further implementation of bulk Raman measurements.

It is an advantage of embodiments of the present invention that low abundant subpopulations of exosomes can be analyzed as compared to analyses which are performed on the overall exosome population level which makes it less likely to find low abundant subpopulations. Indeed, the amount of exosomes derived from diseased cells is typically low compared to vesicles from 'healthy cells' so that detection of altered levels of a single component in a bulk analysis is quite challenging. It is an advantage of embodiments of the present invention that individual exosomes can be identified. This is particularly advantageous in cases where one cell type releases multiple subtypes of exosomes due to which bulk analysis is prone to missing specific subtypes or subtype ratios of vesicles.

It is an advantage of embodiments of the present invention that extracellular vesicles can be identified in a label free manner. Whereas characterization of single extracellular vesicles can be performed for example using labeled antibodies, such an approach requires prior knowledge of the extracellular vesicles since dedicated antibodies need to be developed. The latter can be overcome with the present technique since measurement can be done in a label free manner.

The sample may be a highly diluted sample of extracellular vesicles.

When a plasmonic coating is applied, this may be a homogeneous or non homogeneous coating.

The plasmonic coating may alternatively be built up of a plurality of plasmonic particles which are distributed over the surface of the extracellular vesicle. The coverage of the surface of the extracellular vesicle does not need to be 100%, it is parts of the surface may be not covered by plasmonic particles.

It is an advantage of embodiments of the present invention that they can be used to deepen insight in molecular composition/diversity of the vesicles secreted by a certain cell type.

The plasmonic material, e.g. plasmonic particles, may be functionalized with a positively charged small molecule. It is an advantage of embodiments according to the present invention that the plasmonic particles spontaneously can create a self-assembling shell around an individual cell derived vesicle (e.g. in embodiments of the present invention the plasmonic particles are functionalized with a positively charged small molecule). The positively charged plasmonic particles will create a self-assembling coating around an individual cell derived vesicle if the vesicle is negatively charged. Typically the vesicles are negatively charged.

The functionalized extracellular vesicles may be colloidal stable. It is an advantage of embodiments of the present invention that if the particles stay colloidal particles can be functionally analysed thereafter. Examples of such functionally analysis may be any analysis within the framework of lipidomics, proteomics or transcriptomics.

It is an advantage of embodiments of the present invention that the methods allow to guarantee that individual exosomes can be studied. In some embodiments, these individual exosomes can also be trapped, e.g. by optical trapping although not limited thereto, so as to keep them at a certain position.

Nevertheless, it is to be noticed that the method is not restricted to extracellular vesicles in a colloidal stable dispersion but that the method may also operate on extracellular vesicles that are deposited on the surface of a substrate.

The plasmonic material, e.g. plasmonic particles, may be functionalized using lipophilic or amphiphilic molecules for insertion into the phospholipid bilayer of the extracellular vesicles. It is an advantage of embodiments of the present invention that in general lipids can be used for targeting extracellular vesicles, as this requires no further specification of the extracellular vesicles upfront.

The plasmonic material, e.g. plasmonic particles, may be functionalized using particular targeting ligands, e.g. antibodies, nanobodies, aptamers, etc. for targeting extracellular vesicles.

The plasmonic material, e.g. plasmonic particles, may be formed in the lumen of the extracellular vesicles by incorporating the molecular precursor(s) of said plasmonic material, e.g. particles, into the vesicles.

Pre-formed plasmonic particles can be incorporated in the lumen of extracellular vesicles by inducing pores in the vesicular membrane.

The extracellular vesicles may be, prior to performing said surface enhanced Raman scattering measurements, absorbed to a substrate so as to immobilize them and wherein for performing said surface enhanced Raman scattering measurements, the irradiation beam is scanned over the substrate for individually irradiating the coated extracellular vesicles. It is an advantage of embodiments of the present invention that accurate identification of the extracellular vesicles can be obtained since the extracellular vesicles are immobilized on a substrate. In this way, systematic measurement of the different extracellular vesicles can be performed thus avoiding that certain extracellular vesicles are measured twice.

The extracellular vesicles may be in suspension, during said performing said surface enhanced Raman scattering measurements, whereby said surface enhanced Raman scattering measurements are performed on individual extracellular vesicles when these diffuse through the irradiation beam or may be trapped. Trapping may be performed in the irradiation beam or in another laser beam, i.e. optically, or may be performed in any other suitable manner such as for example hydrodynamically or electromagnetically. It is an advantage that the functionalized extracellular vesicles might be optically trapped to increase the measurement time and therefore the S/N ratio of the SERS spectrum.

It is an advantage of embodiments of the present invention that an easy setup for performing surface enhanced Raman scattering can be used (no scanning of the irradiation beam is required).

The plasmonic particles may be metal based nanoparticles such as silver or titanium particles or wherein the plasmonic particles are carbon-based particles such as graphene particles, graphene oxide particles like graphene oxide nanosheets, carbon nanotubes, carbon nanodots, or fullerenes. It is an advantage of embodiments of the present invention that a variety of plasmonic particles can be used for characterizing the extracellular vesicles.

The plasmonic particles may be gold nanoparticles. It is an advantage of embodiments according to the present invention that well known and stable particles can be used for preparing the extracellular vesicles for individual characterization.

The plasmonic particles may have a diameter within the range 1 to 100 nm, e.g. 5 to 50 nm.

The extracellular vesicles may be exosomes.

After said detecting a surface enhanced Raman spectroscopy signal from said individual extracellular vesicle, the method may comprise comparing said surface enhanced Raman spectroscopy signal with a library of surface enhanced Raman spectroscopy signals for identifying the individual extracellular vesicle. It is an advantage of embodiments of the present invention that based on information of individual extracellular vesicle diagnoses of specific pathologies can be performed. It is to be noticed that deriving the diagnosis is not part of the claimed invention, but is a step that will performed by medical staff after the method as claimed in embodiments of the present invention is performed.

In the method, functionalizing the extracellular vesicles with plasmonic material may comprise binding gold nanoparticles to the surface of the extracellular vesicle or providing at least one gold nanoparticle to the membrane or in the lumen of the extracellular vesicles. The gold nanoparticles may be provided with an additional gold or non-gold metal coating layer. The gold nanoparticles may be coated with a Ag metal layer the Ag metal coating having a thickness of at least 0.5 nm (i.e. the length of the capping agent) but not larger than 100 nm. The gold nanoparticles may be coated with a gold or non-gold metal coating having a thickness of at least 0.5 nm (i.e. the length of the capping agent) but not larger than 100 nm.

The present invention relates to a microfluidic chip for characterization of extracellular vesicles, the microfluidic chip comprising an inlet for obtaining a diluted sample comprising said extracellular vesicles to be characterized, a plasmonic material, e.g. a plurality of plasmonic particles, contactable with said sample for forming a shell of plasmonic material around and/or for providing at least one plasmonic nanoparticle to the membrane, or in a phospholipid bilayer or in the core/lumen of the extracellular vesicles, e.g. introducing one or more plasmonic nanoparticles in the lumen of said individual extracellular vesicles, a microfluidic channel for guiding the functionalised extracellular vesicles to an irradiation position in the microfluidic chip, and the microfluidic chip being adapted for allowing laser radiation in the microfluidic chip at said irradiation position. The microfluidic chip may for example be adapted for operating with an external radiation source, e.g. by providing a window in the chip for receiving the irradiation, or may for example be adapted by having an integrated radiation source in the chip. It is an advantage of embodiments of the present invention that they allow high throughput screening as this allows to screen samples and detect the presence of vesicles from diseased cells which are present in low abundance relative to vesicles from healthy cells.

As indicated above, providing at least one plasmonic nanoparticle may comprise providing a plurality of nanoparticles and providing the at least one plasmonic nanoparticle may comprise attaching a plurality of plasmonic nanoparticles to the surface of the extracellular vesicles and/or may comprise introducing plasmonic nanomaterial on the inside of the exosomes (in the lumen) or may comprise plasmonic nanomaterial being introduced in the phospholipid bilayer.

The present invention furthermore relates to extracellular vesicles comprising a shell of plasmonic material, e.g. nanoparticles or a coating of material, and/or plasmonic material, e.g. nanoparticles, in the core/lumen of the extracellular vesicles or at the surface of the extracellular vesicles or in the phospholipid bilayer. Such a coating of material may provide a homogeneous or non-homogeneous coating.

The at least one nanoparticle may be a plurality of plasmonic particles which are distributed over the surface of the extracellular vesicle, which are in the core/lumen of the extracellular vesicles or at the surface of the extracellular vesicles or in the phospholipid bilayer. The coverage of the surface of the extracellular vesicle does not need to be 100%, it is parts of the surface may be not covered by plasmonic particles.

The plasmonic material may be any of metal based nanoparticles such as gold or silver or titanium particles or the plasmonic material are carbon-based particles such as graphene particles, graphene oxide particles like graphene oxide nanosheets, carbon nanotubes, carbon nanodots, or fullerenes.

The present invention also relates to extracellular vesicles comprising a shell of plasmonic material and/or plasmonic material in the lumen of the extracellular vesicles for use in the diagnosis of diseases causing the production of these extracellular vesicles. The plasmonic material may for example be a plurality of plasmonic nanoparticles or may be a coating such as a chemical vapor deposited coating or a physical vapor deposited coating. It is an advantage of embodiments of the present invention that they can be applied for diagnosis of all diseases wherein a modified exosome/extracellular vesicle is produced by "disease related cells". This is the case for neurodegenerative diseases (e.g. Parkinson disease), for prion diseases (e.g. Creuzfeldt Jakob), for viral infections (e.g. HIV), and for the detection of foreign cells in the body (e.g. each bacterial infection as these organisms also produce extracellular vesicles).

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 24 shows method steps for purifying B16F10- and RBC-derived vesicles in accordance with embodiments of the present invention.

FIGS. 25A and 25B show Theoretical SERS enhancement factors as a function of the percentage coverage of Exosomes with Au NPs for (A) Au NPs at the membrane surface and the (B) average enhancement over the membrane, illustrating features of embodiments of the present invention.

FIGS. 26A and 26B show the near-field response as a function of distance from de NP surface for both (A) AuNP coated with DMAP as well as for (B) AuNP coated with a Ag layer, illustrating features of embodiments of the present invention.

Figure 1:
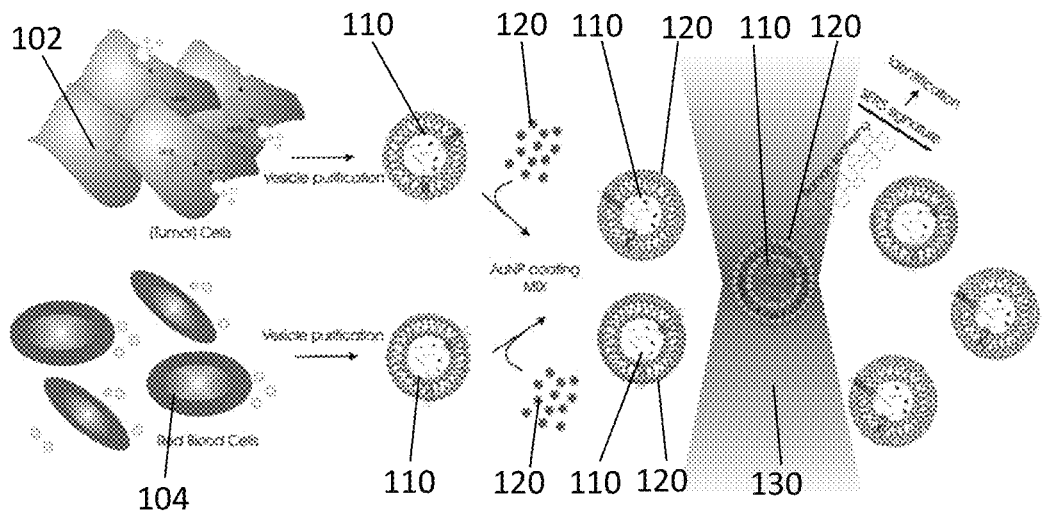
FIG. 1 shows, graphically, different steps of a method for characterizing extracellular vesicles in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect the present invention provides a method for characterizing extracellular vesicles. In the method the extracellular vesicles are characterized at an individual level. The method typically comprises obtaining a sample comprising extracellular vesicles to be characterized. The method also comprises functionalizing the extracellular vesicles using plasmonic material. In some embodiments the plasmonic material may be plasmonic nanoparticles. Nevertheless, the plasmonic material could also be a chemical or physical vapor deposition of the plasmonic material, thus forming a layer coating. The method furthermore comprises irradiating the individual extracellular vesicles and detecting a surface enhanced Raman spectroscopy signal from said individual extracellular vesicle.

According to embodiments of the present invention, the vesicles may be functionalized such that there is physicochemical repelling between them. The latter may advantageously assist in avoiding clustering such that the functionalized vesicles can be studied independently. The physicochemical repelling may be based for example on charge repelling or may correspond with separating particles based on steric effects.

Obtaining a sample comprising extracellular vesicles may be receiving a sample comprising extracellular vesicles. The step of extracting such a sample e.g. from a living creature such as a living human, which is performed prior to said receiving, is typically not part of the claimed method. The sample typically may be vesicles isolated from bodily fluids, e.g. blood, urine, saliva, ascites, . . .

The plasmonic nanoparticles used for functionalizing may be metal based nanoparticles such as gold, silver or titanium particles or wherein the plasmonic particles are carbon-based particles such as graphene particles, graphene oxide particles like graphene oxide nanosheets, carbon nanotubes, carbon nanodots, or fullerenes. Whereas below often the example of gold particles will be used, it is to be noticed that embodiments of the invention thus are not limited thereto.

Functionalizing may be done by creating a coating of plasmonic nanoparticles around the extracellular vesicles. Therefore the extracellular vesicles may be coated with pre-formed nanoparticles or plasmonic particles may be directly formed on the surface of the extracellular vesicles. In case of pre-formed nanoparticles the coating of the extracellular vesicles may be based on hydrophobic interactions. The plasmonic nanoparticles may therefore be functionalized with a single phospholipid or other hydrophobic molecule which inserts in the vesicular membrane hence associating the plasmonic particle to the vesicular surface. In yet another embodiment of the present invention, in case of pre-formed nanoparticles the coating of the extracellular vesicles may be based on charge based interactions. The plasmonic nanoparticles may therefore for example be functionalized with positively charged polymers or positively charged small molecules. These polymers or small molecules may envelop the plasmonic nanoparticles. In some embodiments of the present invention the plasmonic particles may be directly formed on the surface of the extracellular vesicles. It is an advantage of these embodiments of the present invention that no coating molecule is required around the plasmonic particle. Potential interference of the SERS signal by the presence of a coating molecule is thereby avoided. Direct formation of gold nanoparticles may for example be done by adding $HAuCl_4$ to the mixture. Thereby the reduction and therefore the conversion of $HAuCl_4$ to gold nanoparticles may be caused by the presence of proteins on the surface of the extracellular vesicle.

In yet some other embodiments of the present invention the functionalizing of the extracellular vesicles is done intravesicular (i.e. in the core of the extracellular vesicles). The plasmonic nanoparticles (e.g. pre-formed nanoparticles such as for example gold nanoparticles) or molecular precursors (e.g. $HAuCl_4$) migrate through the pores (naturally present in the extracellular vesicles or artificially formed in the extracellular vesicles) into the lumen. It is an advantage of embodiments of the present invention that the plasmonic nanoparticles reside on the inside of the extracellular vesicles and that therefore more and/or alternative information about the structure of the extracellular vesicle can be revealed than in the case the plasmonic nanoparticles are at the surface of the extracellular vesicle.

In some embodiments of the present invention the plasmonic nanoparticles are small (e.g. 5-50 nm, e.g. 10 nm) gold nanoparticles (AuNPs). These small gold nanoparticles are provided around extracellular vesicles or inside the extracellular vesicles (functionalizing of the extracellular vesicles) to enable surface enhanced raman scattering (SERS) measurements of extracellular vesicles.

Alternatively, functionalizing also may be done by creating a layer coating of plasmonic material, e.g. through chemical vapor deposition or physical vapor deposition, instead of through plasmonic nanoparticles.

In embodiments of the present invention the plasmonic material, e.g. nanoparticles, may be functionalized with a positively charged small molecule to create a self-assembling shell around an extracellular vesicle which in that case is negatively charged. The coating around the extracellular vesicle may be an irregularly shaped gold shell. This irregularly shaped shell in combination with laser light allows to create a localized surface plasmon resonance and hence the generation of an enhanced Raman signal of individual vesicles. By functionalizing the extracellular vesicles with plasmonic nanoparticles allows a faster and stronger generation of an extracellular vesicle-derived Raman fingerprint.

In embodiments of the present invention the ratio of plasmonic nanoparticles (e.g. AuNPs) over vesicles is chosen such that the above mentioned characteristics can be obtained. By selecting the optimal ratio, in embodiments of the present invention, extracellular vesicles from different cells can be discriminated (e.g. from 2 different cells). In embodiments of the present invention the ratio of plasmonic nanoparticles over vesicles is dependent on the size of the plasmonic nanoparticle and the size, hence surface area, of the isolated vesicle. It ranges for example between 2 and 100000, e.g. between 90 and 20 000, e.g. between 200 and 10000, e.g. between 600 and 1200. The upper limit may alternatively for example be determined by the following equation:

$$\overline{\frac{AuNP}{EXO}} = \frac{\sum_{i=1}^{n}[S_{EXO,i} \cdot \eta / SS_{AuNP}]}{n}$$

with n as the total amount of vesicles, $S_{EXO,i}$ as the surface of a vesicle i, $\eta$ the maximum packing density of a sphere with a diameter of 10 nm and $SS_{AuNP}$ as the surface of the section occupied by one AuNP. It will be clear that the formula can be adapted mutates mutandis to other types of particles.

In embodiments of the present invention the functionalization of the extracellular vesicles (the binding of the coating) may be done by using lipid functionalized plasmonic nanoparticles (e.g. AuNPs) for insertion into the extracellular vesicle phospholipid bilayer, or by using antibody-functionalized plasmonic nanoparticles (e.g. AuNPs), or by direct synthesis of the plasmonic nanoparticles (e.g. AuNPs).

In an exemplary embodiment of the present invention a gold nanoparticle based shell is deposited on the surface of exosomes derived from cancerous and healthy cells to enhance the Raman signal while maintaining individual vesicles in suspension.

Figure 27:
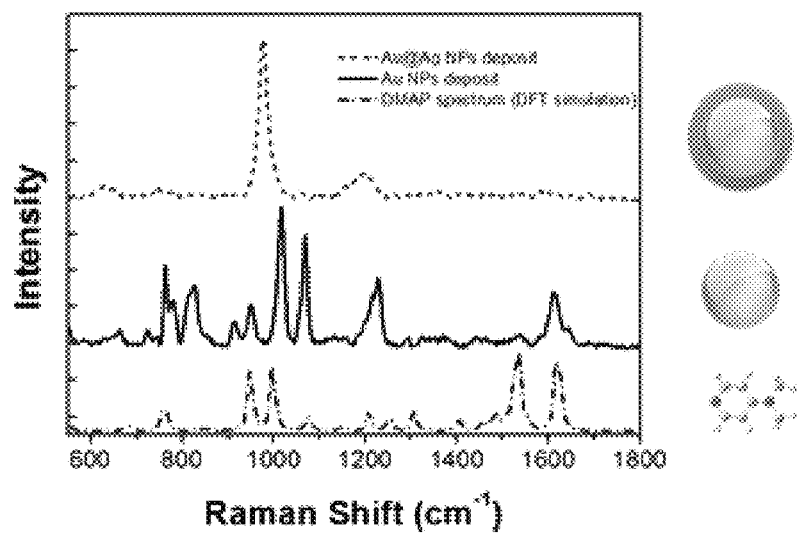
FIG. 27 shows from top to bottom SERS spectrum of Au@Ag NPs; SERS spectrum of Au; Ab-initio calculations of the Raman spectra of DMAP (the SERS spectra were measured with an irradiating wavelength of 785 nm), illustrating features of embodiments of the present invention.

In some embodiments, functionalizing the extracellular vesicles with plasmonic material comprises binding gold nanoparticles to the surface of the extracellular vesicle, the gold nanoparticles being coated with an additional plasmonic metal layer to shield the interfering Raman signal of the AuNP coating molecule (FIG. 27). The gold nanoparticles may for example be coated with a Ag metal layer. The thickness of the additional plasmonic metal layer may be between at least 0.5 nm and 100 nm, e.g. between at least 0.5 nm and 50 nm.

As indicated above, in embodiments of the present invention an individual extracellular vesicle is irradiated and a surface enhanced Raman spectroscopy signal is detected from said individual extracellular vesicle. It is thereby an advantage of embodiments of the present invention that only one extracellular vesicle is irradiated at a time. The irradiation may be performed using a laser beam. In some embodiments, the irradiation may be performed by a laser beam being part of a lab-on-chip system comprising also all other elements for performing the method.

In embodiments of the present invention, upon detection of the surface enhanced Raman spectroscopy signal, the signal is analysed for identifying individual extracellular vesicles. This may be done based on a look-up table, an algorithm, a theoretical calculation or based on neural networks, etc. In one particular example, a look up table is setup making use of Partial Least Squares-Discriminant Analysis (PLS-DA) for identifying individual extracellular vesicle (e.g. to distinguish between two types of vesicles even in mixed samples).

FIG. 1 gives a schematic overview of the steps of a method in accordance with embodiments of the present invention. In the example vesicles 110 are generated by tumor cells 102 and by red blood cells 104. These vesicles 110 are coated with AuNPs 120, after which the individual extracellular vesicles 110 are irradiated with a laser beam 130. The individual extracellular vesicle thereby generates a surface enhanced Raman spectroscopy signal which is detected in a next step in embodiments according to the present invention.

In an exemplary embodiment of the present invention 'miniature' SERS-substrates around individual exosomes are envisioned by deposition of small gold nanoparticles (AuNP) on the exosomal surface forming a gold, irregularly shaped nanoshell enabling the generation of a strong Raman signal.

In an alternative embodiment of the present invention the functionalized extracellular vesicles (e.g. the gold coated extracellular vesicles) remain in suspension and SERS spectra are recorded of individual extracellular vesicles that diffuse through and potentially are temporarily optically trapped in the Raman laser beam. Embodiments of the present invention may comprise an opto-microfluidic device, to accelerate spectra collection from individual vesicles making a high throughput screening system possible.

In embodiments of the present invention the functionalization of the extracellular vesicles may be self-assembling (e.g. self-assembling shell formation of AuNPs) allowing it to be used in future, automated (chip based) systems.

By way of illustration, embodiments of the present invention not being limited thereto, experimental results are described below. These illustrate features and advantages of embodiments of the present invention.

A mouse derived, B16F10 melanoma cell line was used as a model for carcinogenic cells and primary, human RBC as a model for healthy cells as the latter is likely to be the most abundant in blood samples. In the present example, B16F10 melanoma cells (ATCC) were cultured in Dulbecco's Modified Eagle Medium (DMEM, Invitrogen), supplemented with 2 mM glutamine, 10% heat-inactivated fetal bovine serum (FBS, Hyclone) and 100 U/mL penicillin/streptomycine (Invitrogen) at 37° C. in a humidified atmosphere containing 5% $CO_2$. For purification of exosomes, in the present example, cells were first washed with phosphate-buffered saline (PBS, Invitrogen) and the cell medium was replaced with vesicle depleted medium. Vesicle depleted medium was prepared by ultra-filtrating full cell medium through a 300 kDa filter (Millipore) using an Amicon stirred cell setup (Millipore) under three bar nitrogen pressure to remove bovine extracellular vesicles. Cells were incubated for 24 to 30 hours after which the conditioned cell medium is harvested for exosome purification.

Red blood cells (RBC) were purified from blood from a healthy volunteer as described below. Briefly, blood was collected in K2EDTA coated tubes (Venosafe®) and spun at 1500 g for 15 minutes within 10 minutes after blood collection. RBC were retained, washed twice and suspended in Ringer buffer (150 mM NaCl, 5 mM KCl, 2 mM $CaCl_2$, 1 mM $MgCl_2$, 2 mM $NaH_2PO_4$, 10 mM HEPES, 10 mM Glucose, pH=7.2) for 2 days at 37° C. while shaking.

Vesicles derived from B16F10 melanoma cells and RBC were purified from conditioned cell medium or Ringer buffer, respectively by differential centrifugation followed by density gradient ultracentrifugation (possible method steps therefore were illustrated in FIG. 24). In a first step 2410, conditioned cell medium/Ringer buffer was centrifuged for 10 minutes at 300 g and in a second step 2420, 10 minutes at 3000 g. In a following step 2430, the supernatant was concentrated by ultrafiltration using a 30 kDa filter (Millipore) in an Amicon stirred cell setup (Millipore) under nitrogen pressure. In a following step 2440 the concentrated sample was centrifuged at 10 000 g for 10 minutes using a SW55ti rotor (Beckman instruments) and the supernatant was placed on top of an iodixanol (Optiprep®, Axis-Shield) based density gradient. The gradient was produced according to the manufacturer's instruction. Briefly, 1 ml of different iodixanol dilutions (12.5%, 25%, 37.5% and 50% in 250 mM sucrose, 1 mM EDTA, 10 mM Tris-HCl buffer; pH=7.4) were carefully laid underneath one another using a 21 G needle. The samples were then centrifuged at 150 000 g for 15 hours (step 2450). Next, the gradient was fractionated per 0.5 ml, diluted 10× in ultrapure water and centrifuged at 150 000 g for 150 minutes (step 2460). Finally, the pellet was washed 1 more time and resuspended in ultrapure water (step 2470). The fraction containing the exosomes was further used for characterization and Raman spectroscopy experiments.

Using techniques as described above, it is an advantage of some embodiments of the present invention, the present invention not being limited thereby, that contamination from protein complexes or residuals of kit reagents is avoided because this contamination interferes with the surface enhanced Raman spectroscopy signal from the individual extracellular vesicle. Moreover, other less stringent purification protocols (i.e. ultracentrifugation and commercial precipitation kits) suffer from limited purity due to co-purification of extracellular vesicle independent proteins and nucleic acids, which might shield the AuNP from interacting with the extracellular vesicles.

Nevertheless, it is to be understood that other types of purification protocols can also be used in embodiments of the present invention, and that the above protocol is only given by way of illustration.

Figure 2:
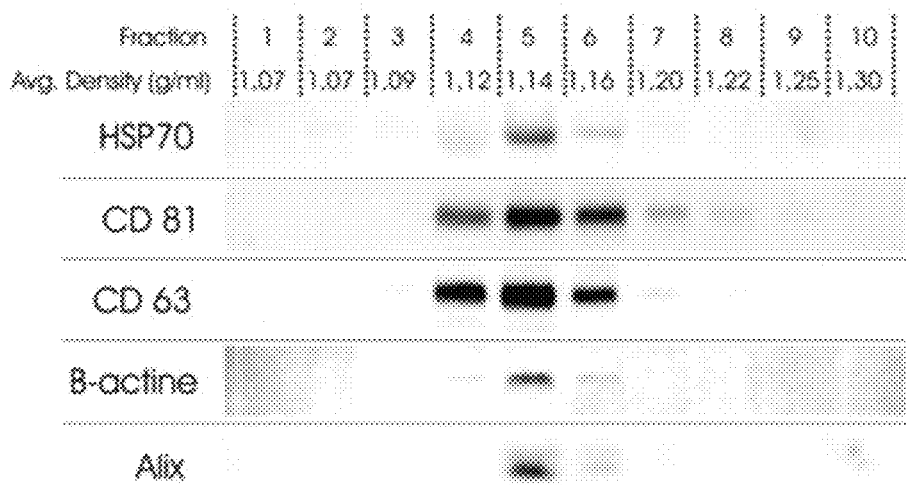
FIG. 2 shows the characterization of B16F10 melanoma-derived exosomes using immune-blotting against exosomal markers Alix, CD63, HSP 70, CD81, and β-actin on different density fractions.

After density gradient ultracentrifugation, in the present example, the fraction containing the exosomes was determined by immune-blotting against typical exosome associated protein markers (Alix, HSP70, CD81, CD63, β-actin) on each fraction of the density gradient. The result thereof is illustrated in FIG. 2. In this respect, fraction 5 contains the highest amount of exosomal markers. In the example the density fractions were obtained after overnight density gradient ultracentrifugation of B16F10 melanoma derived conditioned medium. In FIG. 2 for each fraction the average density is reported ($g/cm^3$). The average density of fraction 5 was 1.14 g/ml which corresponds with earlier reports on the typical buoyant density of exosomes. In order to determine the density fraction containing the exosomes, pelleted vesicles were resuspended in ice cold RIPA buffer (Sigma-Aldrich) mixed with MS-SAFE protease and phosphatase inhibitor cocktail (Sigma-Aldrich) and vortexed. Next, the samples were sonicated for 10 minutes and centrifuged at 13 000 g for 5 minutes. For protein separation, samples were diluted in 2× laemmli buffer (Bio-Rad) with our without 5% 2-mercaptoethanol (Sigma-aldrich), heated at 95° C. for 5 minutes and loaded on a 10% mini-protean TGX precasted gel (Bio-Rad). The polyacrylamide gel was run at 100 V for 60 minutes in running buffer (25 mM Tris-200 mM Glycine—0.1% SDS). The blotting was done on an immune-blot® PVDF 0.2 μm membrane (Bio-Rad) at 100 V for 90 minutes in blotting buffer (25 mM Tris-200 mM Glycine—20% Methanol—0.05% SDS). The blot was blocked for 1 hour using 3% BSA, 0.1% Tween20 in PBS buffer (Invitrogen). Next primary antibodies were incubated overnight at 4° C. on a shaker. After washing the blots with blocking buffer they were incubated with the secondary antibody conjugated to HRP for 1 hour at room temperature. Visualization was done using the SuperSignal West Dura chemiluminscent kit (Thermo-Scientific) in combination with a VersaDoc™ imaging system (Bio-Rad).

In this example the purified exosome concentration and size was determined by light scattering based single particle tracking using a NanoSight LM10 instrument (Malvern instruments Ltd.) equipped with a 405 nm laser. Prior to analysis, the concentrated vesicles were diluted in HEPES buffer (pH 7.4; 20 mM) to obtain a concentration in the range of 1.0 to $9.0 \times 10^8$ particles/ml to guarantee reliable measurements. Movies of 60 seconds were recorded and analysed with the NTA Analytical Software version 2.3.

Size and zeta potential of exosomes and exosome coated with AuNPs were measured by dynamic light scattering (DLS) using a Zetasizer Nano ZS (Malvern instruments Ltd.), equipped with Dispersion Technology Software.

In this example, also cryo-transmission electron microscopy was applied to the sample. For each exosome (AuNP) sample, 3.5 μL is applied to a 300 mesh quantifoil grid and incubated for 30-60 seconds. Next, excess buffer is removed by blotting the grids for 3 seconds using a Whatmann 1 filter paper and the sample is snap frozen by plunging in liquid ethane at a temperature of −180° C. and stored in liquid nitrogen until visualization. Next, the samples are transferred to a Gatan 914 cryoholder and imaged at low dose conditions (max 1000 electrons per $nm^2$) at −177° C., using a JEOL JEM1400 TEM equipped with a 11 Mpxl Olympus SIS Quemesa camera.

For further characterising, in the present example the exosomes were also fluorescently labelled and confocal microscopy is applied to the exosomes. Purified B16F10- and RBC-derived vesicles are incubated for 15 minutes at 37° C. with Vibrant® DiD (Invitrogen) or PKH67 (Sigma), respectively (final dye concentration=5 μM; in Diluent C (Sigma)). Next, non-incorporated dye and diluent C were removed using exosome spin columns (MWCO 3000) (Invitrogen) pre-incubated with ultrapure water according to the manufacturer's instructions.

For further characterising, the labeled exosomes were mixed with AuNPs in the indicated ratios and visualized using a swept field confocal microscope (LiveScan SFC, Nikon Belux, Belgium). The exosomes are irradiated with 488 nm or 647 nm laser light and images are recorded with an iXon Ultra EMCCD camera (Andor). Particle detection is done and the B16F10:RBC ratio (B16F10 over RBC derived vesicles) is determined for each mixture by particle counting in at least 20 individual recordings at different spatial locations.

In this exemplary study gold nanoparticles (AuNP) coated with 4-dimethylaminopyridine (DMAP) are prepared as described briefly below. A HAuCl$_4$ aqueous solution was added to a tetraoctylammonium bromide in toluene solution under gentle stirring. Next, NaBH$_4$ was added to the mixture. After 30 minutes the toluene phase was separated from the aqueous phase and washed 3 times using H$_2$SO$_4$, NaOH and ultrapure water. Equal volumes of the AuNP in toluene solution and an aqueous DMAP solution were mixed and left to equilibrate for 1 hour. During this period the AuNP transfer from the organic toluene phase to the aqueous phase and exchange the tetraoctylammonium bromide coat for a DMAP coating. Next, the aqueous phase is separated from the toluene phase.

Figure 22:
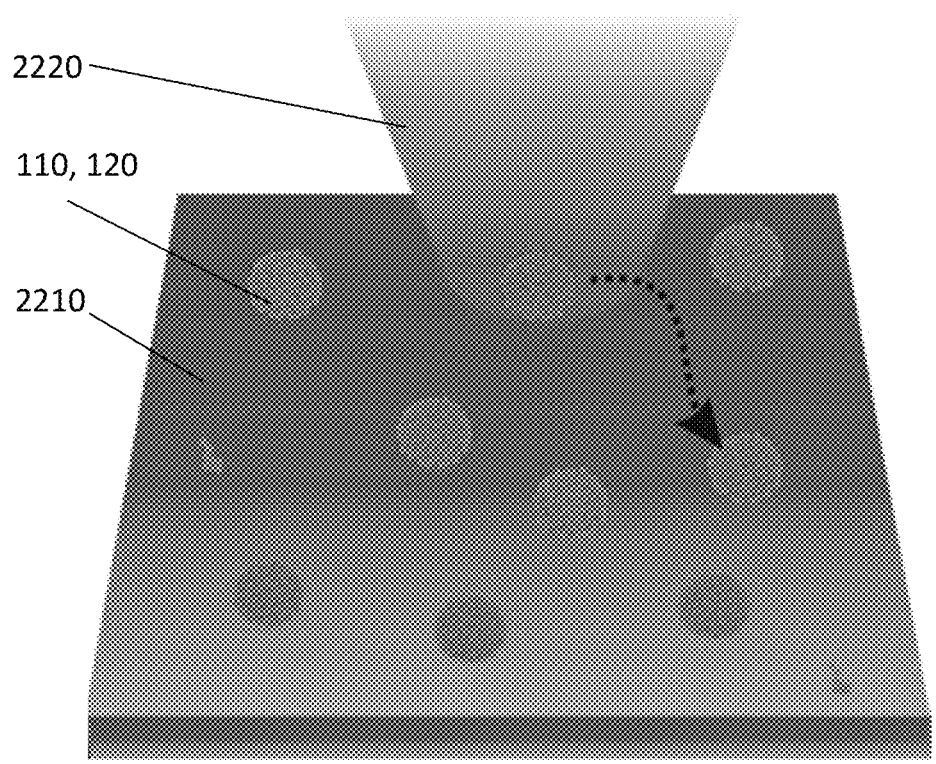
FIG. 22 shows a laser focus which can be moved over a substrate on which extracellular vesicles are immobilized, in accordance with embodiments of the present invention.

In this exemplary study of the present invention exosomes were mixed with 4-dimethylaminopyridine (DMAP) coated AuNP in the indicated ratio and left for 10 minutes at room temperature. Next, samples were diluted in ultrapure water to ≤5×10$^7$ vesicles per μl. A 60 μl droplet of the sample was placed on a quartz substrate and SERS spectra were recorded using an inVia confocal Raman microscope (Renishaw, UK) equipped with a 60× WI lens (NA=1, Nikon) and a 785 nm laser using a 10 second integration time and 15 mW power. Alternatively, a Raman microscope (Zeiss) equipped with a piezo-scanner (P500, physick instrumente) and a 785 nm laser focused through a 60× WI lens (NA=1, Nikon) was used (integration time 500 ms). The spectra were acquired with a thermoelectrically cooled CCD camera (DU401ABV, Andor). All spectra are recorded at different locations in the sample as illustrated in FIG. 22.

In this exemplary study the obtained data was pre-processed as described by Marro et al. in 'Molecular Monitoring of Epithelial-to-Mesenchymal Transition in Breast Cancer Cells by Means of Raman Spectroscopy', *Biochim Biophys Acta,* 1843 (2014), 1785-95]. To assess the ability of Raman spectroscopy to discriminate RBC and B16F10 melanoma derived exosomes, Partial Least Squares-Discriminant Analysis (PLS-DA) was performed using the PLS toolbox from Eigenvector Research in MatLab. Cross-validation analysis was computed by Venetian blinds (10 splits and one sample per split). The number of retained LVs is chosen to minimize the root mean square error of cross validation (RMSECV) curves. Also, a Multivariate Curve Resolution-Alternative Least Squares algorithm is used to analyze the spectra.

Figure 3:
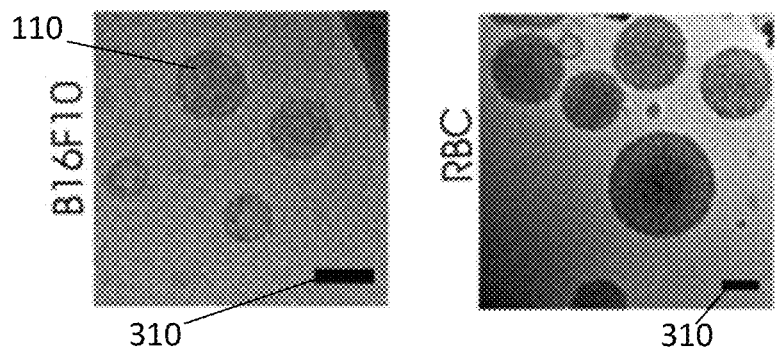
FIG. 3 shows cryo-TEM images of pure vesicular substrates; the left image shows B16F10 derived vesicles, the right image shows RBC derived vesicles.
Figure 4:
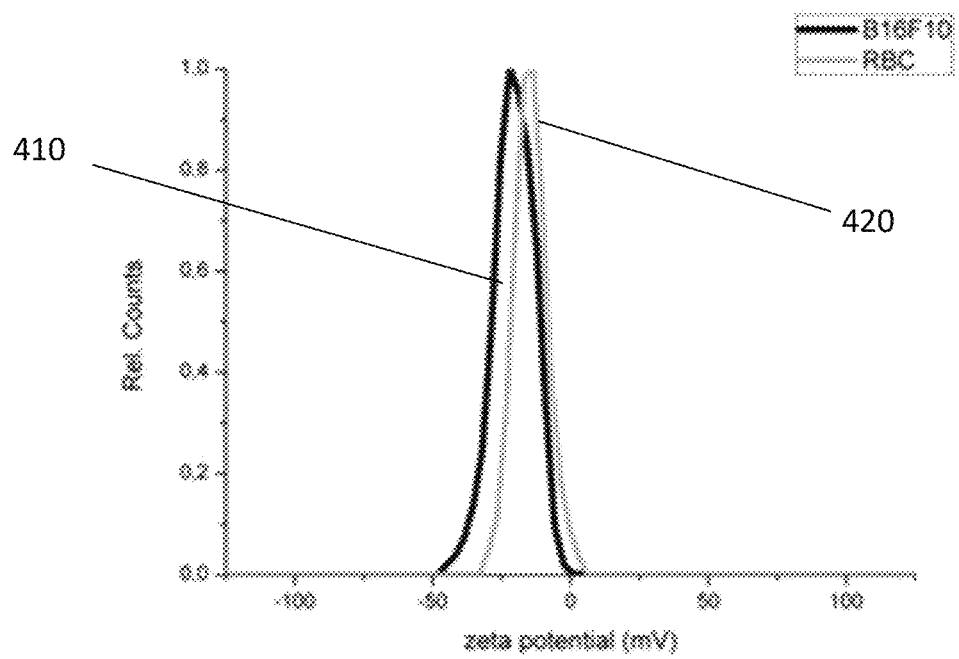
FIG. 4 shows the Zeta potential for B16F10 melanoma derived purified exosomes and for RBC derived purified exosomes.
Figure 5:
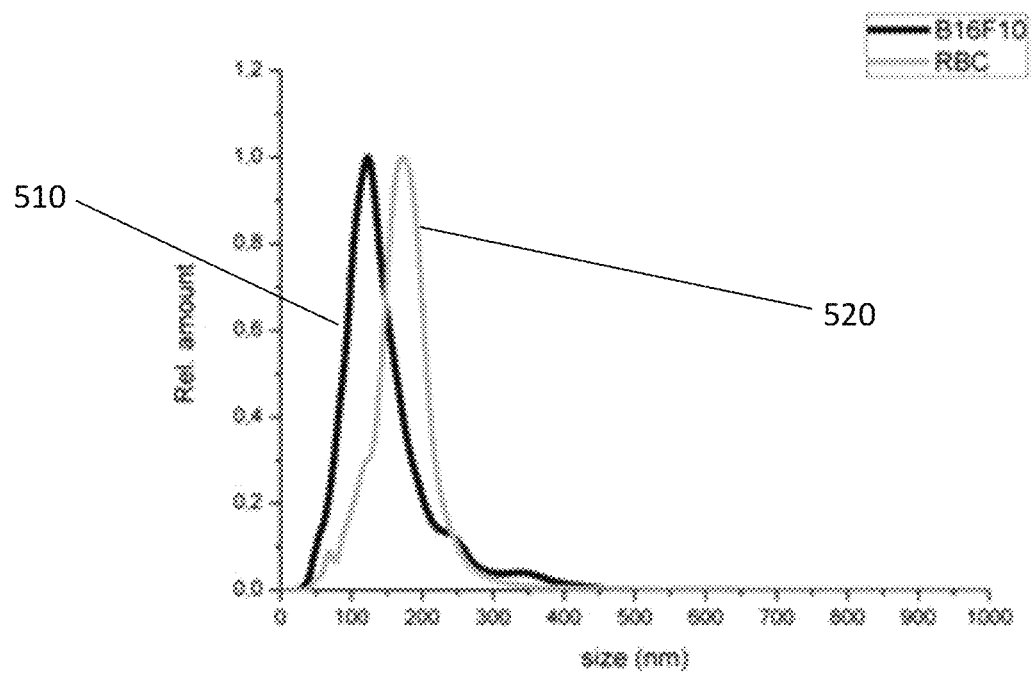
FIG. 5 shows the size distribution of B16F10 melanoma derived purified exosomes and of RBC derived purified exosomes.

After isolation, the exosomal pellet was suspended in ultrapure water (Millipore) and analysed for size and zeta potential by nanoparticle tracking analysis and dynamic light scattering, respectively. In the exemplary embodiment of the present invention the B16F10 melanoma derived exosomes have an average hydrodynamic diameter of approx. 0.12 μm. The RBC derived vesicles are slightly bigger with an average size of approx. 0.17 μm. Cryo-TEM images of B16F10 melanoma (left) and RBC derived (right) purified exosomes are shown in FIG. 3. The scale bar 310 in this figure indicates 100 nm. Both types of vesicles in this example have a negative surface charge (see zeta potential in FIG. 4). FIG. 4 shows the Zeta potential for B16F10 melanoma derived purified exosomes (the left black curve 410) and for RBC derived purified exosomes (the right grey curve 420). FIG. 5 shows the size of B16F10 melanoma derived purified exosomes (the left black curve 510) and of RBC derived purified exosomes (the right grey curve 520). The Zeta potential and the size are determined by dynamic light scattering and by nanoparticle analysis respectively. The cryo-TEM images of FIG. 3 confirm the presence of membranous structures in the purified samples. For both B16F10 and RBC derived vesicles the cryo-TEM images show pure vesicular concentrates.

Figure 6:
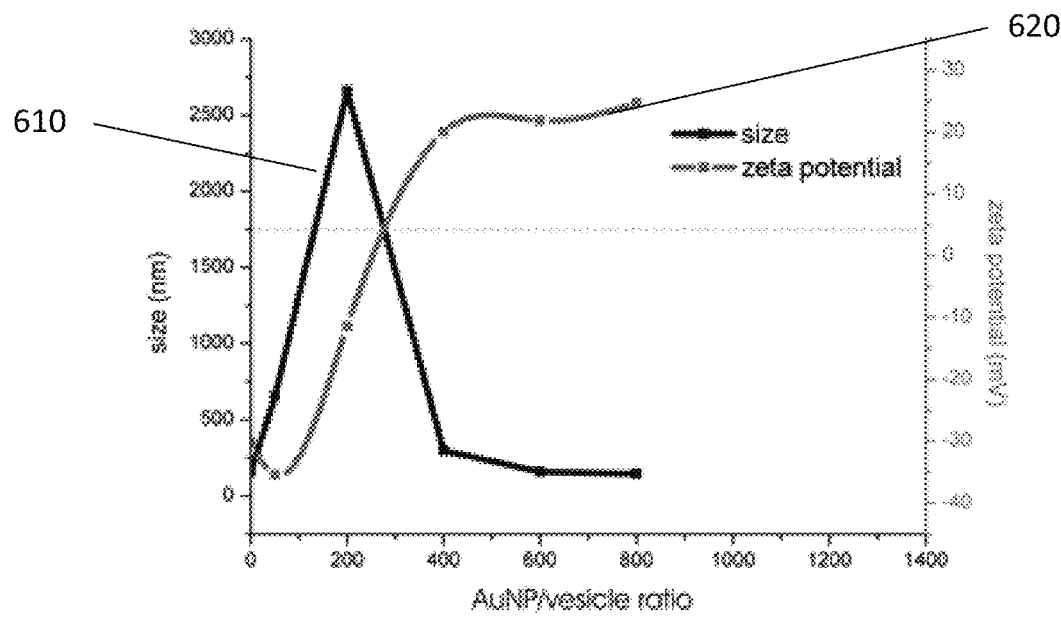
FIG. 6 shows the average size and zeta potential of AuNP coated B16F10 melanoma derived exosomes, in accordance with embodiments of the present invention, for different AuNP/vesicle ratios as indicated in the x-axis.
Figure 7:
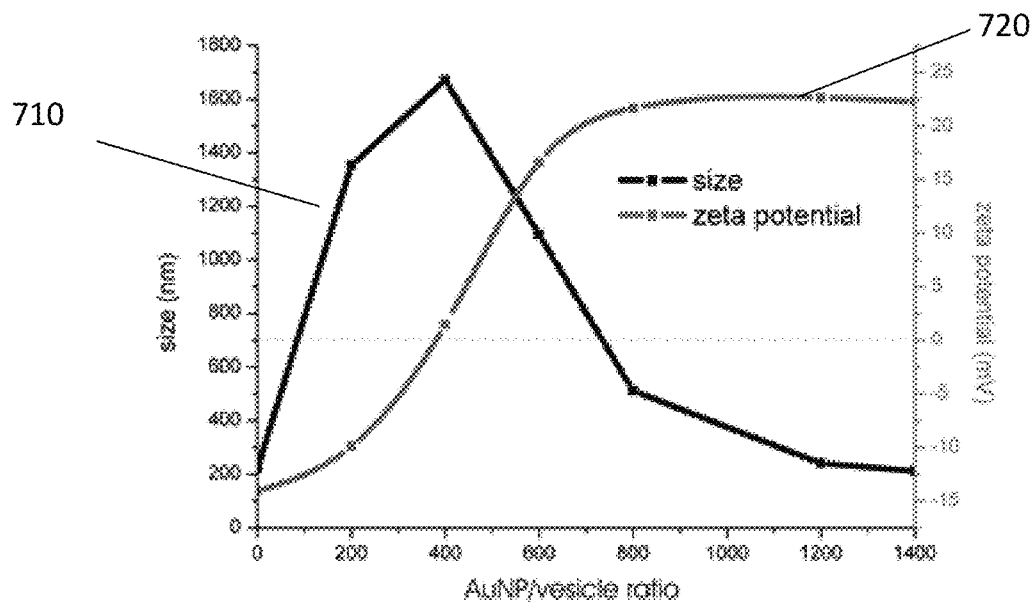
FIG. 7 shows the average size and zeta potential of AuNP coated RBC-derived vesicles, in accordance with embodiments of the present invention, for different AuNP/vesicle ratios as indicated in the x-axis.
Figure 8:
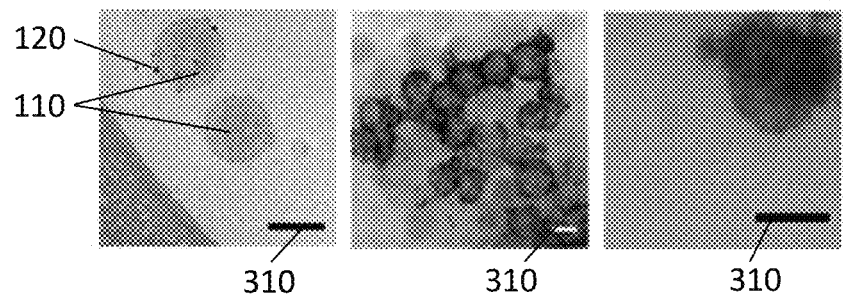
FIG. 8 shows cryo-TEM images of AuNP coated B16F10 derived exosomes in accordance with embodiments of the present invention.
Figure 9:
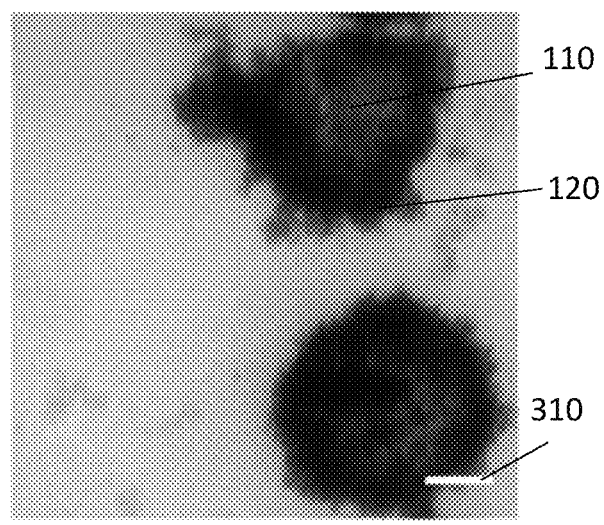
FIG. 9 shows a cryo-TEM of AuNP coated RBC-derived exosomes in accordance with embodiments of the present invention (AuNP/vesicle ratio of about 1300).
Figure 19:
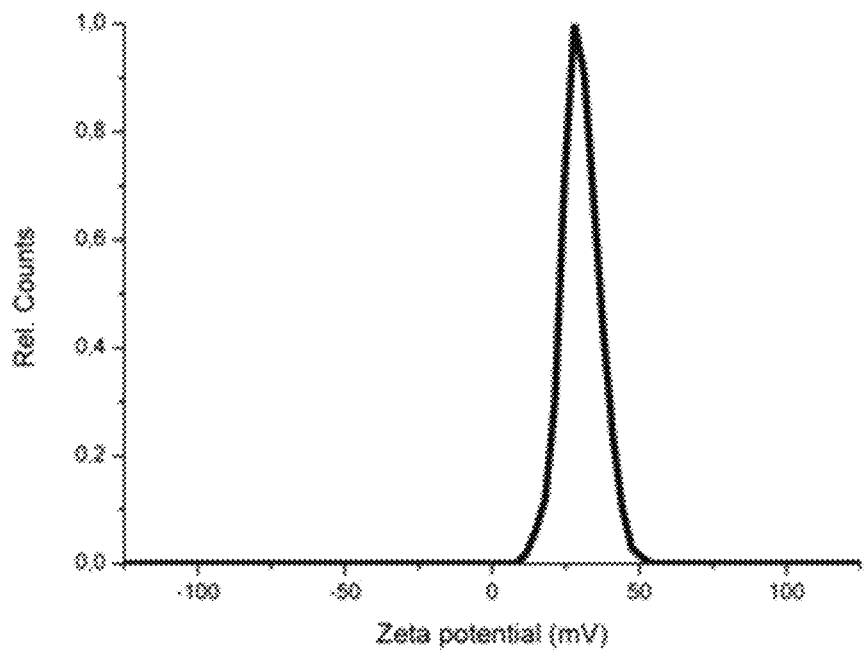
FIG. 19 shows the Zeta potential of DMAP coated AuNPs.
Figure 20:
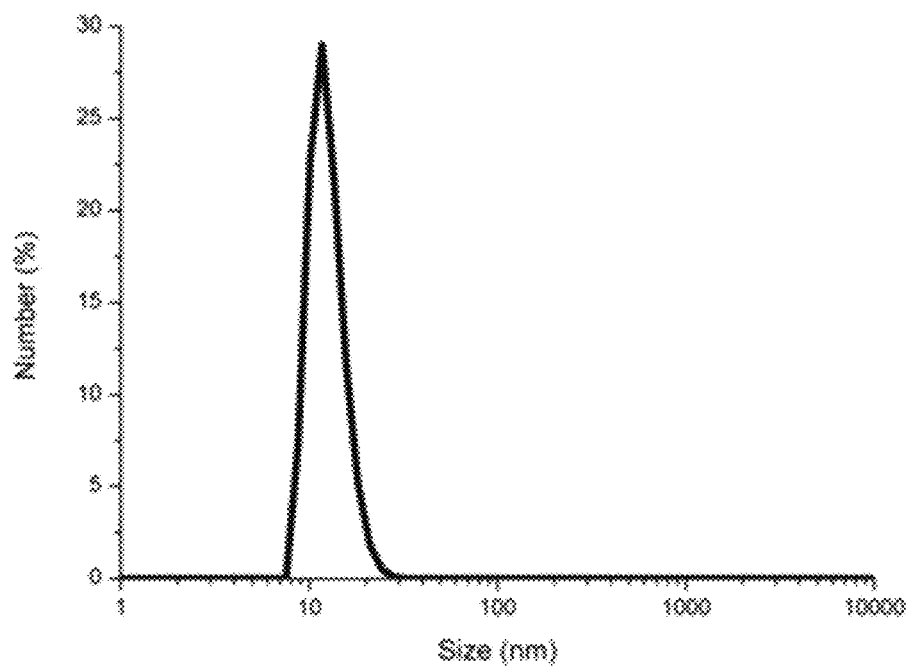
FIG. 20 shows the size distribution of DMAP coated gold nanoparticles determined by dynamic light scattering.

In the present study the plasmonic particles were functionalized with a positively or negatively charged small molecule. The protocol of the functionalization of the extracellular vesicles (e.g. the coating of the exosomes) with plasmonic nanoparticles (e.g. gold nanoparticles) may for example be optimised for functionalization while maintaining a stable colloidal vesicle suspension. The coating of the exosomes may for example be based on the electrostatic adsorption of cationic (FIG. 19), 10 nm (FIG. 20) AuNP onto the anionic vesicles. FIG. 19 shows the Zeta potential of DMAP coated AuNPs and FIG. 20 shows the size of DMAP coated gold nanoparticles determined by dynamic light scattering. In an exemplary experiment of the present invention the AuNP are mixed with vesicles at increasing particle concentration ratios. FIG. 6 shows the average size 610 and zeta potential 620 of AuNP coated B16F10 melanoma derived exosomes for different AuNP/vesicle ratios as indicated in the x-axis. FIG. 7 shows the average size 710 and zeta potential 720 of AuNP coated RBC derived vesicles. As can be seen from FIG. 6 and FIG. 7 an increase in the ratio of AuNP/vesicles causes a shift in the overall size and zeta potential of the vesicle mixture. Moreover, as an additional confirmation of the charge based interaction between AuNPs and exosomes, cryo-TEM images of AuNP 120 coated B16F10 derived exosomes 110 with different AuNP/vesicle ratios are recorded (FIG. 8). The left image corresponds with a AuNP/vesicle ratio of 10, the middle image a AuNP/vesicle ratio of 100, and the right image with a AuNP/vesicle ratio of 1000. The scale bar 310 in each of the images indicates 100 nm. By adding more AuNPs the zeta potential becomes gradually more positive. When the zeta potential approaches zero, the vesicles tend to aggregate due to the loss of mutual repulsion. This observation is confirmed by cryo-TEM as low amounts of AuNP per vesicle (~10) clearly show that the AuNP associate on the exosomal surface. Here, individual vesicles with a few AuNP on their surface are formed while other vesicles do not house any AuNP. By increasing the amount of AuNP per vesicle (~100) the majority of the vesicles contain AuNP. Yet, their surface is not fully coated and furthermore the exosomes aggregate. Adding even more AuNPs resulted in a positively charged, stable colloidal suspension of AuNP coated exosomes. At least around 600 AuNP per B16F10 vesicle (FIG. 6) and 1200 AuNP per RBC vesicle (FIG. 7) are required to obtain a colloidal stable suspension. The fact that more AuNP per vesicles are needed to coat the RBC compared to the B16F10 melanoma vesicles is in perfect accordance with the surface of the RBC derived vesicles being exactly 2 times larger (FIG. 5). For this higher ratio cryo-TEM imaging shows complete coating of the B16F10 melanoma derived vesicles with AuNP. Likewise, AuNP coating of RBC derived vesicles in the respective ratio provides complete surface coverage (FIG. 7 and FIG. 9). Moreover, the obtained ratios are comparable with the theoretical calculations on the amount of AuNP needed to cover the entire vesicular surface in a monolayer. The theoretical average amount of AuNPs needed to coat an entire vesicular surface in a monolayer is given by the following formula:

$$\frac{AuNP}{EXO} = \frac{\sum_{i=1}^{n}[S_{EXO,i} \cdot \eta / SS_{AuNP}]}{n}$$

with n as the total amount of vesicles, $S_{EXO,i}$ the surface of a vesicle i, η the maximum packing density of a sphere with a diameter of 10 nm and $SS_{AuNP}$ as the surface of the section occupied by one AuNP. It is to be noticed that the coverage with Au NPs does not need to be complete in order to obtain a strong enhancement. The latter will also be illustrated further below.

FIG. 9 shows a cryo-TEM of AuNP 120 coated RBC derived exosomes 110 (AuNP/vesicle ratio of about 1300). The scale bar 310 indicates 100 nm.

Figure 10:
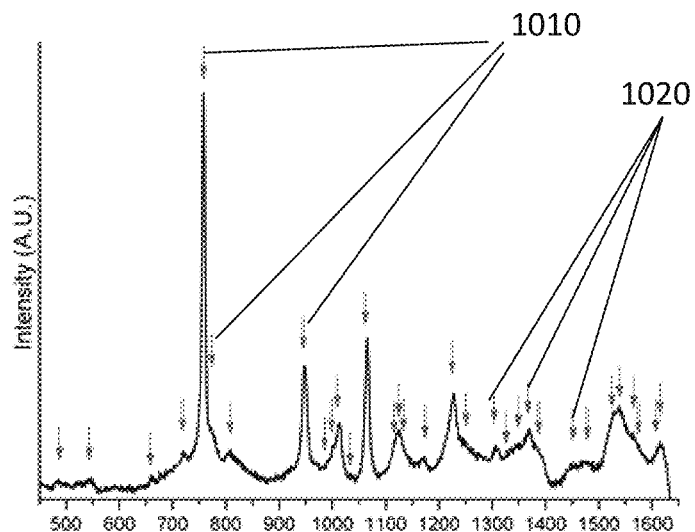
FIG. 10 shows the surface enhanced Raman spectroscopy signal from an individual RBC-derived extracellular vesicle in accordance with embodiments of the present invention.
Figure 11:
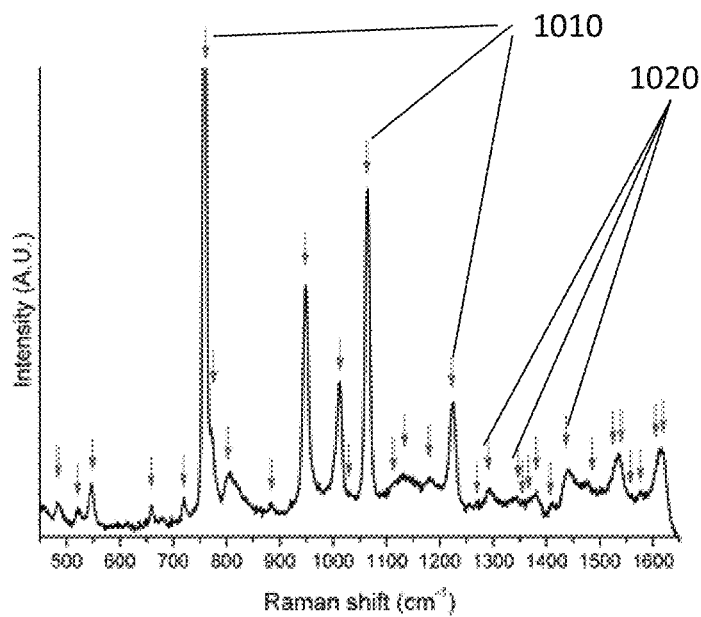
FIG. 11 shows the surface enhanced Raman spectroscopy signal from an individual melanoma derived extracellular vesicle in accordance with embodiments of the present invention.
Figure 23:
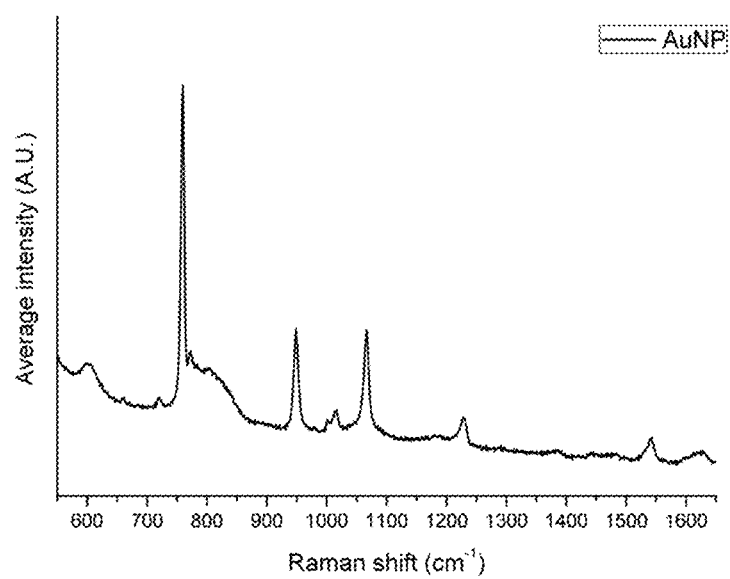
FIG. 23 shows the surface enhanced Raman spectroscopy signal from an individual AuNP alone in accordance with embodiments of the present invention.

In the present study the close packing of AuNP on the vesicular surface allows to generate a SERS spectral fingerprint. This is illustrated in FIG. 10 and FIG. 11. These drawings show the spectra recorded from individual AuNP coated exosomes by moving the laser's focal plane to different refractive spots on the quartz substrate. The horizontal axis shows the Raman shift ($cm^{-1}$), the vertical axis is the intensity (in arbitrary units). This is done for RBC derived vesicles (FIG. 10) and B16F10 melanoma derived vesicles (FIG. 11) separately, as well as for AuNPs alone (FIG. 23). The recorded spectra contain peaks arising from the DMAP coating of the AuNP (markers without arrow 1010) as well as additional peaks from exosomal biomolecules (markers with arrow 1020). The same sample without the presence of AuNP was not able to generate a clear Raman signal using the indicated settings. It is an advantage of embodiments of the present invention that the identified peaks can be associated with their molecular origin (e.g. classes of biomolecules: lipids, proteins, nucleic acids, carbohydrates). Examples of DMAP bands are 759 $cm^{-1}$, 949 $cm^{-1}$, 1065 $cm^{-1}$, 1227 $cm^{-1}$, 1540 $cm^{-1}$. Typical bands for the exosomal components are 1123 $cm^{-1}$ (lipids+proteins), 1172 $cm^{-1}$ (proteins), 1307 $cm^{-1}$ (proteins+lipids), 1366-1370 $cm^{-1}$ (phospholipids+carbohydrates), 1445 $cm^{-1}$ (lipids+proteins), 1572 $cm^{-1}$ (nucleic acids).

Figure 12:
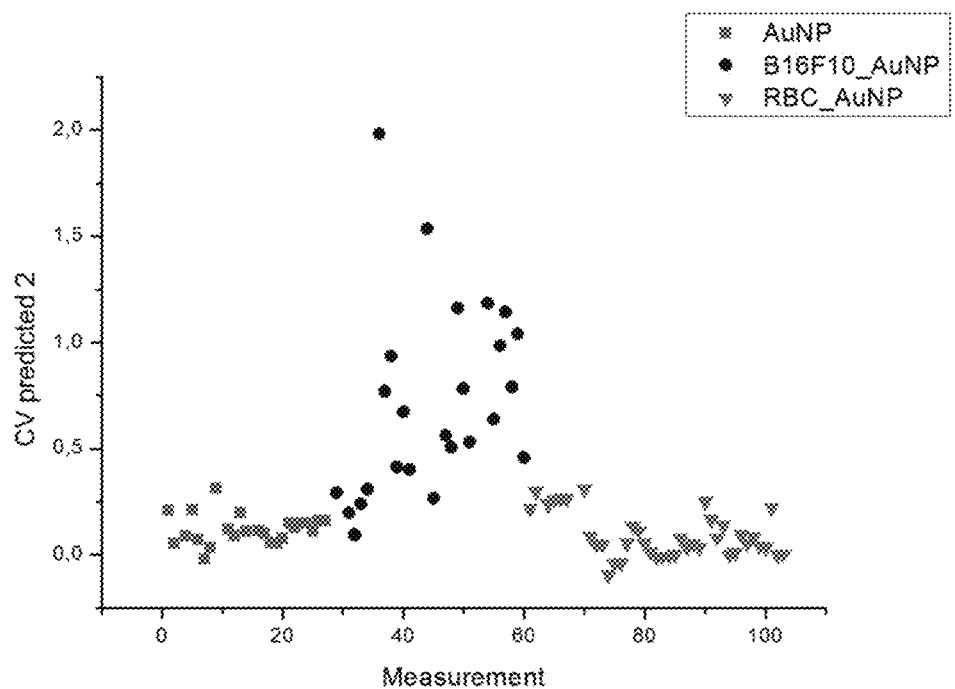
FIG. 12, FIG. 13, and FIG. 14 represent the partial least square discriminant analysis on spectra of parted samples for only AuNPs, for only AuNP coated B16F10 derived vesicles and for AuNP coated RBC derived vesicles respectively, in accordance with embodiments of the present invention.
Figure 13:
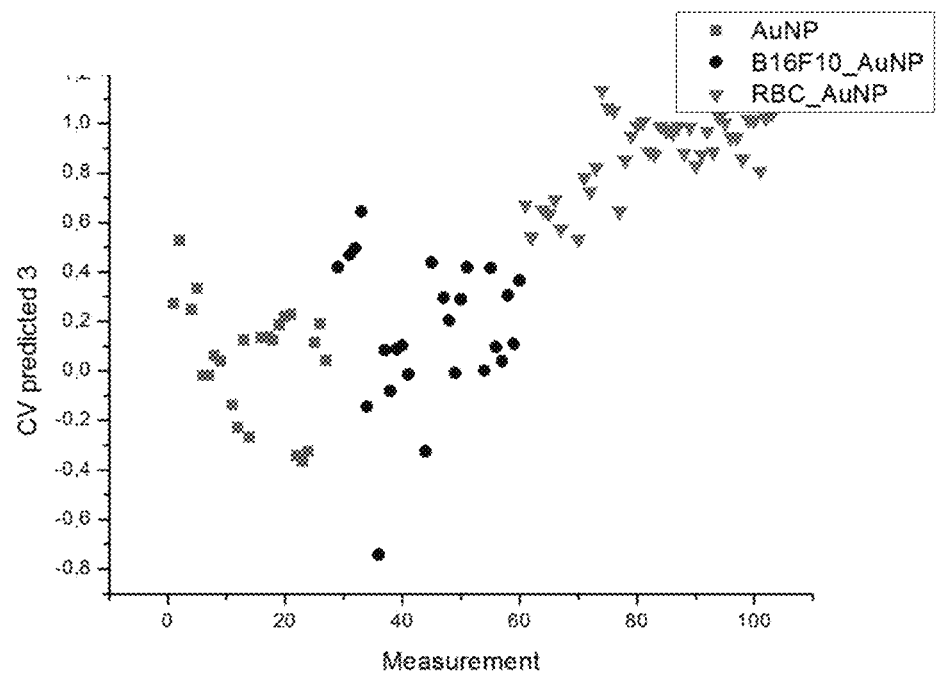
Figure 14:
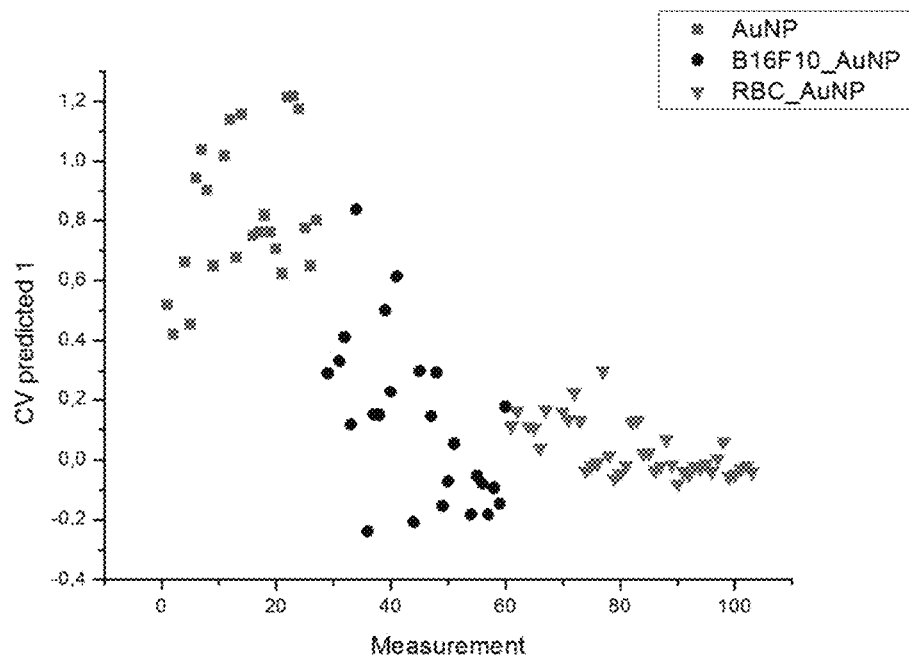
Figure 15:
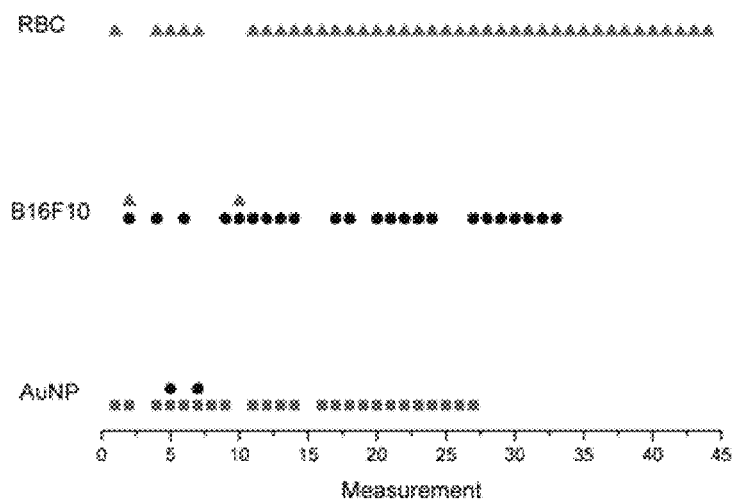
FIG. 15 shows the classification of the spectra of parted samples in accordance with embodiments of the present invention.

In the present study PLS-DA was applied for identifying the individual extracellular vesicle. Thereby a PLS-DA model was built and the obtained surface enhanced Raman spectroscopy signal from an individual extracellular vesicle is coupled with statistical analysis. In the present study this is done to discriminate RBC from B16F10 melanoma derived exosomes. In this example the model spectra derived from AuNP, AuNP coated B16F10 derived vesicles and AuNP coated RBC derived vesicles were included. First, the specificity and sensitivity of the model to discriminate among the different types of vesicles was assessed by cross-validation. A sensitivity of 0.958, 0.880, 0.951 and specificity of 0.955, 0.954 and 0.980 for AuNP, B16F10 and RBC derived exosomes respectively are obtained. Results of these models are represented in FIG. 12, FIG. 13, FIG. 14 and FIG. 15. FIG. 12, FIG. 13, and FIG. 14 represent the partial least square discriminant analysis on spectra of parted samples. FIG. 12 corresponds with the calculated response in class2 (corresponding with B16F10_AuNP) FIG. 13 with the calculated response in class3 (corresponding with RBC_AuNP) and FIG. 14 with the calculated response in class1 (corresponding with AuNP) recorded with an integration time of 10 seconds. The calculated response (on the Y-axis) corresponds with the scores given by the PLS-DA model for each sample that allows the model to allocate a spectrum to one of the three classes of samples. These results are shown for different individual SERS spectra (on the X-axis). FIG. 15 shows the classification of the spectra of parted samples: AuNP (squares), B16F10 derived vesicles coated with AuNP (circles) and RBC derived vesicles coated with AuNP (triangles) after cross-validation using leave-one-out cross validation methodology. The x-axis shows the measurement number. As can be seen from FIG. 15 only two of the individual spectra from the RBC derived vesicles coated with AuNP were wrongly classified as B16F10 and only two of the spectra from the B16F10 derived vesicles were wrongly classified as AuNP.

Figure 21:
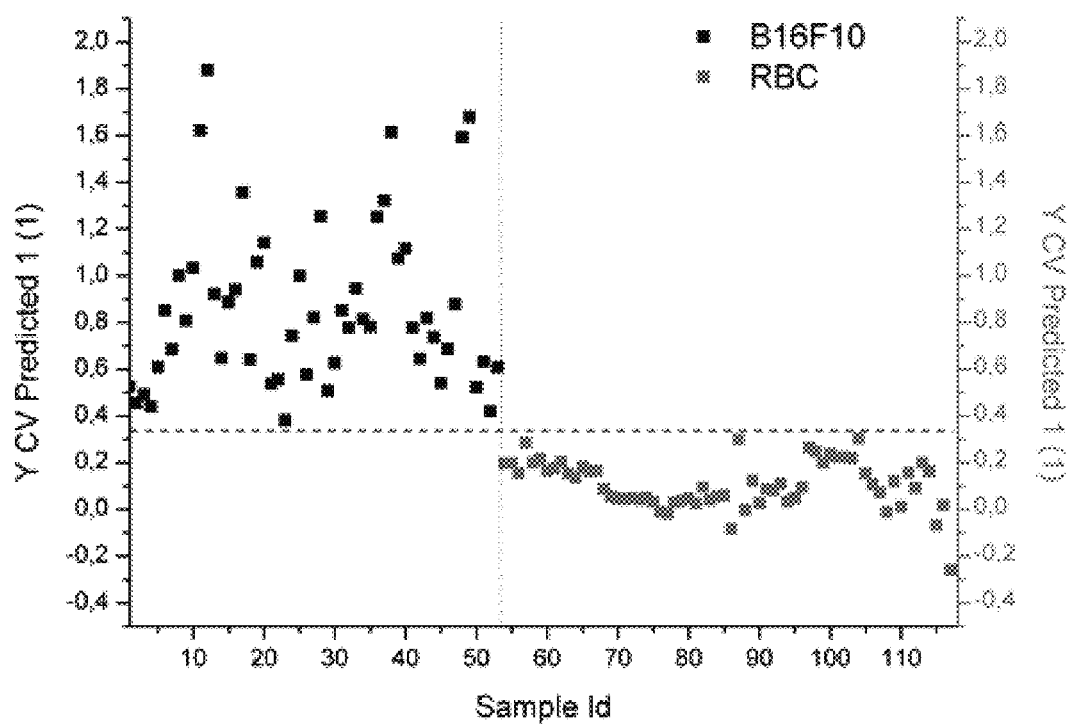
FIG. 21 shows the PLS-DA analysis results on the surface enhanced Raman spectroscopy signal from individual extracellular vesicles, in accordance with embodiments of the present invention.

FIG. 21 shows the analysis results on the surface enhanced Raman spectroscopy signal from individual extracellular vesicles. AuNP coated vesicles from B16F10 and AuNP coated vesicles from RBC were used as samples. In this exemplary embodiment of the present invention the Raman spectrometer allows short acquisition times (500 ms). The acquisition time of 500 ms is a limitation of the particular Raman instrument used and not of the method according to embodiments of the present invention. Analysis of the obtained data is performed using the PLS-DA model. As can be seen from FIG. 21 it is an advantage of embodiments of the present invention that they are able to separate between samples based on their SERS fingerprint (i.e. based on their detected surface enhanced Raman spectroscopy signal). FIG. 21 shows on the horizontal axis the sample Id and on the vertical axis the calculated response for class 1. The squares on the left of the vertical dotted line represent vesicles from B16F10 and the squared on the right of the vertical dotted line represent vesicles from RBC. The horizontal dashed line allows to separate the samples based on their SERS fingerprint. The B16F10 results are in the top left quadrant, the RBC results are in the bottom right quadrant.

Figure 16:
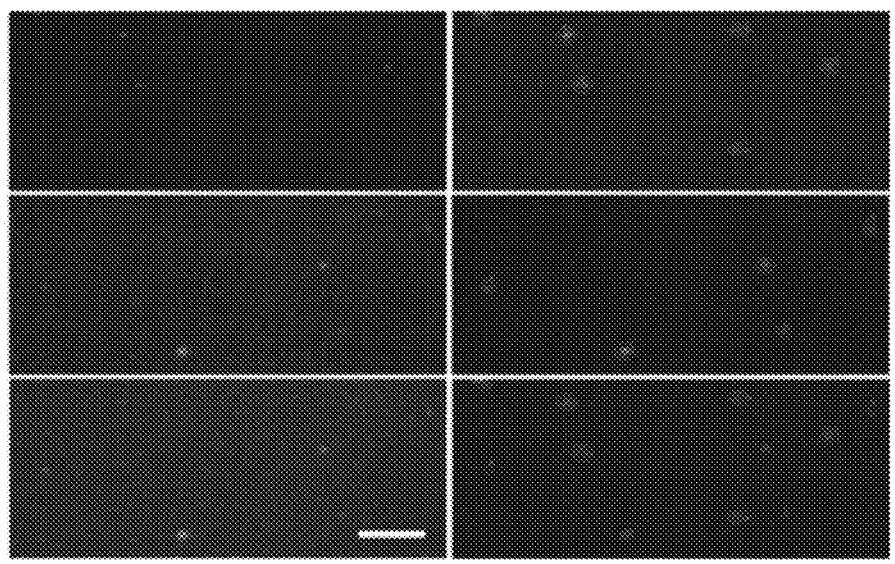
FIG. 16 shows confocal images of a mixture of AuNP coated, fluorescently labelled RBC- and B16F10 melanoma derived exosomes.
Figure 17:
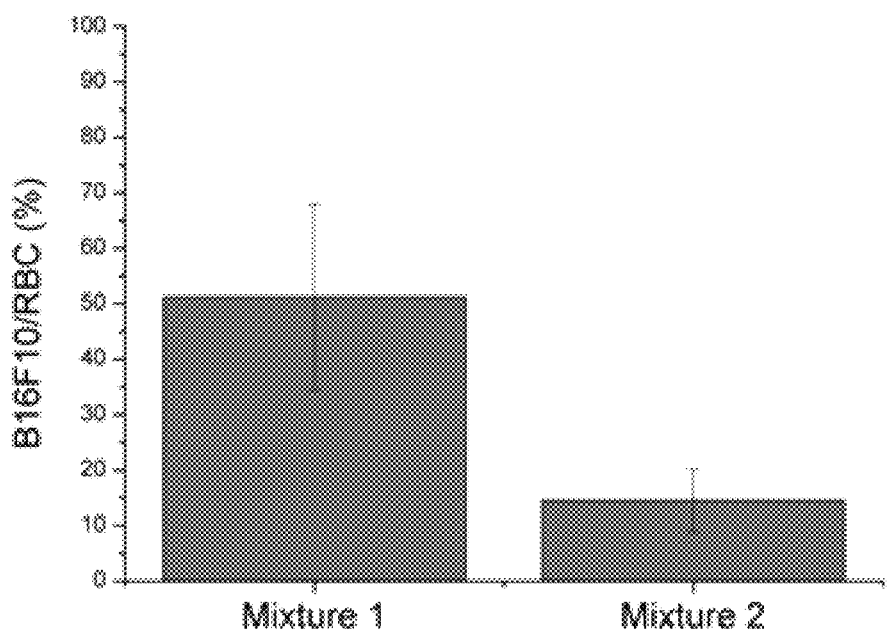
FIG. 17 shows the percentage B16F10 melanoma derived vesicles for two different mixtures of RBC- and B16F10 melanoma derived exosomes based on fluorescence particle counting.
Figure 18:
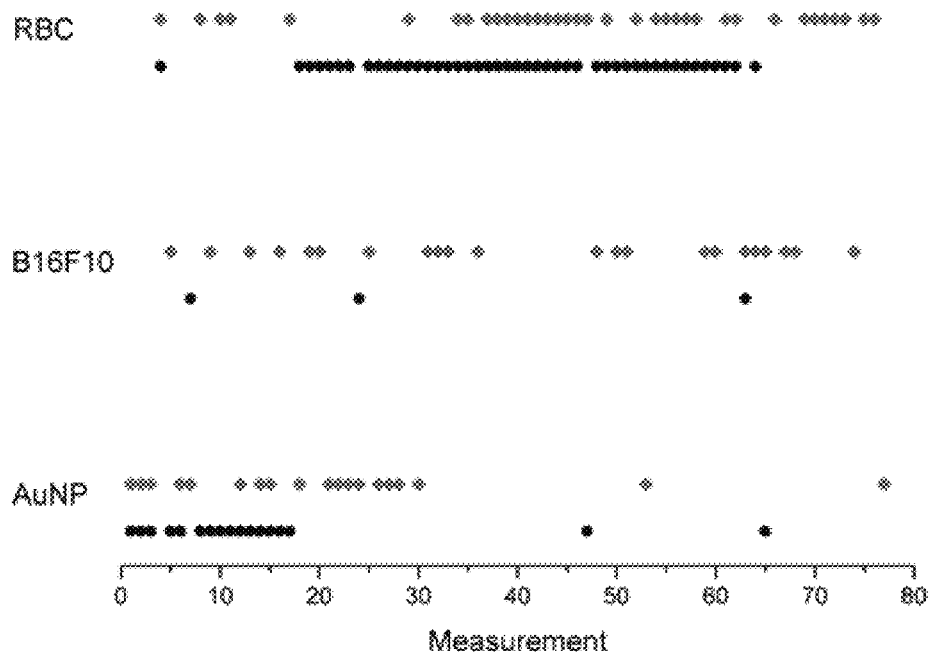
FIG. 18 shows the classification of the spectra of SERS measurements on individual exosomes, executed on two B16F10:RBC exosomal mixtures, in accordance with embodiments of the present invention.

In the following example mixtures of AuNP functionalized cancer- and healthy-cell derived exosomes were prepared at different ratios. This setup more closely resembles the in vivo situation where cancerous exosomes need to be detected in patient samples containing a variety of exosome types. To determine the exact ratio of both types of vesicles in the mixtures, the vesicles were fluorescently labelled with lipophilic dyes (RBC=green; B16F10=red) and coated with AuNP. The suspension was placed on a microscopy cover slip and confocal microscopy images were recorded. With in-house developed particle detection software the number of green and red fluorescent spots were counted. The top row in FIG. 16 shows the fluorescent labelled RBC derived exosomes. The middle row shows the fluorescent labelled B16F10 melanoma derived exosomes. The bottom row shows an overlay of both. The left column shows a representative confocal image of mixture 1, the right column shows the same image with particle location. From the analysis it was calculated that mixture 1 contained 51±17% cancerous exosomes and mixture2 contained 15±6% cancerous exosomes. This result is illustrated in FIG. 17. As can be seen from images of FIG. 16 it is an advantage of embodiments of the present invention that the two types of AuNP coated vesicles do not agglomerate with one another as no co-localization of spots in the images of the top row and spots in the images of the middle row can be seen. In the same example identical mixtures were prepared for SERS measurements in accordance with an embodiment of the present invention and without fluorescent labels. In the examples shown the functionalized extracellular vesicles (e.g. the gold coated extracellular vesicles) were adsorbed to a substrate 2210 so as to make sure they are immobilized and then the laser focus 130 can be moved from extracellular vesicle 110 to extracellular vesicle 110 to capture their SERS spectra. An example thereof is illustrated in FIG. 22. For each mixture between 60 and 80 spectra were recorded at different locations in the sample, each time focusing on anther AuNP coated vesicle (as illustrated in FIG. 22). With the PLS-DA model each spectrum was assigned to one of the following groups: AuNP, RBC derived exosomes or B16F10 derived exosomes. 38% and 6% cancerous vesicles are retrieved in mixture 1 and 2, respectively (FIG. 18). FIG. 18 shows PLS-DA of SERS measurements, in accordance with embodiments of the present invention, executed on two B16F10:RBC exosomal mixtures. Each point represents an individual spectrum allocated to one of the three classes (AuNP, AuNP coated B16F10 exosomes or AuNP coated RBC exosomes). Mixture 1 measurement results are represented by a rhombus, mixture 2 measurement results are represented by a circle. A part of the spectra are found to originate from unbound AuNP. It can be seen that the SERS based values reasonably correspond to what is expected based on the fluorescence measurements. The latter illustrates that for example cancerous vesicles in more complex mixtures can be identified.

The detected surface enhanced Raman spectroscopy signal thus allows identification of vesicles from different cellular origin in a quantitative measure. When using embodiments of the present invention, this can be done faster than using time-consuming 'omics' (e.g. genomics, proteomics, metabolomics) studies. The samples advantageously are not measured in bulk but on a single vesicle level. This allows to identify exosomes from different origins even when present at a low concentration in the mixture.

In the present example a MCR-ALS (Multivariate Curve Resolution Alternating Least Squares) algorithm was used to deconvolve molecular components from the mixed samples. In an exemplary embodiment of the present invention three main components are deconvolved and assigned to spectra from AuNP, RBC and B16-F10, respectively. The results are in agreement with the ones obtained with PLS-DA in terms of spectra grouping and classification.

FIG. 24 shows the schematic representation of a protocol used to purify exosomes from conditioned cell medium in accordance with an embodiment of the present invention.

In a second aspect the present invention provides a microfluidic device for characterization of extracellular vesicles. The microfluidic chip comprises an inlet for obtaining a sample comprising said extracellular vesicles to be characterized. The microfluidic chip comprises plasmonic material, e.g. a plurality of plasmonic particles, contactable with said sample for forming a shell of plasmonic material, e.g. plasmonic particles, around and/or for entering in the lumen of said individual extracellular vesicles. The microfluidic chip moreover is adapted for allowing laser radiation in the microfluidic chip. It may for example comprise a window for allowing laser radiation in the microfluidic chip or it may comprise an integrated laser, e.g. such as in a lab-on-chip system. The system also may comprise a microfluidic channel for guiding the functionalized extracellular vesicles to an irradiation position in the chip. The extracellular vesicle may be bound to a substrate in front of the window or they may pass by the window. Other features may correspond with features as described in the first aspect.

In a third aspect the present invention provides extracellular vesicles comprising a shell of plasmonic material, e.g. plasmonic nanoparticles, and/or plasmonic material in the pores of the extracellular vesicles. The plasmonic nanoparticles may be metal based (e.g. gold, silver, titanium), the may be carbon based (e.g. graphene, graphene oxide particles like graphene oxide nanosheets, carbon nanotubes, carbon nanodots, or fullerenes). Other features may be as described for the first aspect.

By way of illustration, embodiments of the present invention not being limited thereto, some results are discussed, illustrating effects of providing an additional plasmonic metal coating on the plasmonic nanoparticles. In the following results the use of an additional silver coating on gold nanoparticles are discussed.

The presence of surfactants and small organic molecules as capping agents restricts the application of Au nanoparticles and nanostructures as SERS substrates for biosensing as the signals of the capping agent could interfere with the identification of the compounds of interest. The results discussed below illustrates the use of SERS substrates for the identification of ELVs using Au NPs attached to the membrane of the exosomes as templates for the deposition of a Ag layer. As the layer of silver is deposited onto the ligands of the Au NPs and as the outermost layer dominates the interaction with light, Au@Ag core-shell NPs are good candidates for SERS studies.

The optical response of Au and Au@Ag NP functionalized exosomes were computed using the Generalized Multiparticle Mie Theory (GMM). In the calculations performed the NPs were excited by a plane wave with an incidence pointing vector (propagation direction) normal to the surface. For the GMM calculations of the near field optical properties a multipolar expansion order of 10 was used. The GMM code is restricted to applications in homogeneous media, therefore an effective medium approximation was used to account for the interface between the exosome membrane and the aqueous environment. It was considered that particles were immersed in a dielectric environment with an effective refractive index of $n_{eff}=1.37$, which was calculated considering the surface of the NP in contact with the membrane and to media and the refractive index of the membrane (nr=1.45) and water (nr=1.33). The dielectric functions tabulated by Palik for Au and Ag were employed in the calculations. As the size of the particles is small enough, the optical behavior could be considered in the quasi-static approximation limit. According to this, for Au@Ag core-shell NPs, the Maxwell-Garnett effective medium theory was used to calculate the effective permittivity of those NP.

The theoretical electromagnetic SERS enhancement, for small Raman shifts, scales with the fourth power of the field enhancement. Considering that the fourth power approximation is valid, the electromagnetic field enhancement factor (EFEF) is defined by:

$$EFEF = |\Gamma(\omega)|^2$$

$$|\Gamma(\omega)| = \left(\left|\frac{E(\omega)}{E_0(\omega)}\right|\right)^2$$

where $|\Gamma(\omega)|$ is the square of the enhanced electric field generated at the frequency of the incident radiation ($\omega$). For the calculation of the different EFEFs the functionalized exosome (120 nm in diameter and a maximum number of 668 NPs) was considered as a superposition of planes with different number of nanoparticles. For each plane the near field optical properties were calculated and the reported value in each case is the average of the different planes.

The trends in the near field optical properties of some selected configurations of coated exosome like vesicles (ELVs) containing different number of Au NPs (100%, 80%, 60%, 40% and 20% cover) and Au@Ag NPs (20% cover) as calculated by rigorous electrodynamics modeling using GMM theory are discussed. In all cases, the simulations were performed so as to determine the average electromagnetic field enhancement experienced by the exosome membrane (FIGS. 26A and 26B). FIGS. 26A and 26B illustrate a schematic illustration of the near-field response as a function of distance from the NP surface. The maximum enhancement it is generated at the metal surface ($EFEF_{MAX}$) followed by an exponential decay. For molecules that are located at a certain distance from the metal surface an upper limit must be considered in the enhancement that it is related to the distance to the metal surface, for this purpose only the values of enhancement lower than a particular value N must be considered ($\Gamma \leq N$). The illustration shows the different enhancements factors that can be considered to evaluate the SERs response of the exosome membrane in the case of A) DMAP-functionalized Au NPs and B) Au@Ag NPs.

The variation of the SERS electromagnetic field enhancement factor (EFEF) and the distribution of the near field with respect of the cover of Au NPs was examined and the comparison with the optical properties after the generation of a layer of Ag onto the Au NPs for low covering (20%) was studied. For big molecular structures that are located within a few nanometers from the metal surface, but not in direct contact with it, the important parameter that correlates with the measured SERS signals is the maximum field enhancement factor at the location of the molecule ($EFEF_{MAX}$) and the average electromagnetic field enhancement factor along the molecule ($EFEF_{Average}$). The EFEF at a particular frequency $(F(\omega))^2$ is defined by the fourth power of the ratio between the maximum field (E) in the cluster of NPs and the incident field (Eo). FIGS. 25A and 25B show the different EFEF calculated values for the different conditions specified above. FIG. 25A shows $$EFEF_{MAX \atop \Gamma \leq N} = \text{theoretical}$$

enhancement considering the forth power of the enhanced field at the incident frequency (w) for Au NPs at the membrane surface whereas FIG. 25B shows $$EFEF_{Average \atop \Gamma \leq N} = \text{theoretical}$$

enhancement considering the average enhancement over the membrane.

The values clearly depict a decrease in the EFEF as a function of the NPs % cover and it can be observed that a maximum limit is reached approximately at 40% cover. The fact that the theoretical simulations predict a decrease in the EFEF as a function of the cover it is not intuitive as it would be expected that a higher number of nanoparticles generate more hot spots and consequently higher signals. Nevertheless, two features of the near field distribution deserved to be remarked: Firstly, the molecules that would be analyzed through the SERS signals are not located in the hot spots of maximum enhancement. These "hot spots" in every case have at least 2 orders of magnitude greater than the enhancement in the regions where the membrane it is located. Secondly, as the number of hot spots increases the electromagnetic enhancement spatial distribution is mainly located in these active regions and less electromagnetic field enhancement is spread to the region in which the membrane of the exosomes it is located. This features generate a disadvantage, as the maximum enhancement is achieved in the region where the coating molecule (i.e., DMAP) it is located. As a strategy to overcome the signals of the coating agent of the Au NPs, a layer of Ag was generated onto the functionalized Au NPs for 20% covering.

FIG. 27 shows the comparison of the experimental SERS spectrum of a deposit of Ag@Au NPs and Au NPS onto a glass slide. From top to bottom a SERS spectrum of Au@Ag NPs, a SERS spectrum of Au and Ab-initio calculations of the Raman spectra of DMAP can be seen. The SERS spectra were measured irradiating at $\lambda=785$ nm. As can be observed in the Figure the spectrum obtained after the generation of the Ag layer it is less complex than in the case of Au NPs (less number of peaks). The peaks attributed to DMAP disappeared after the generation of the Ag layer.

Figure 28:
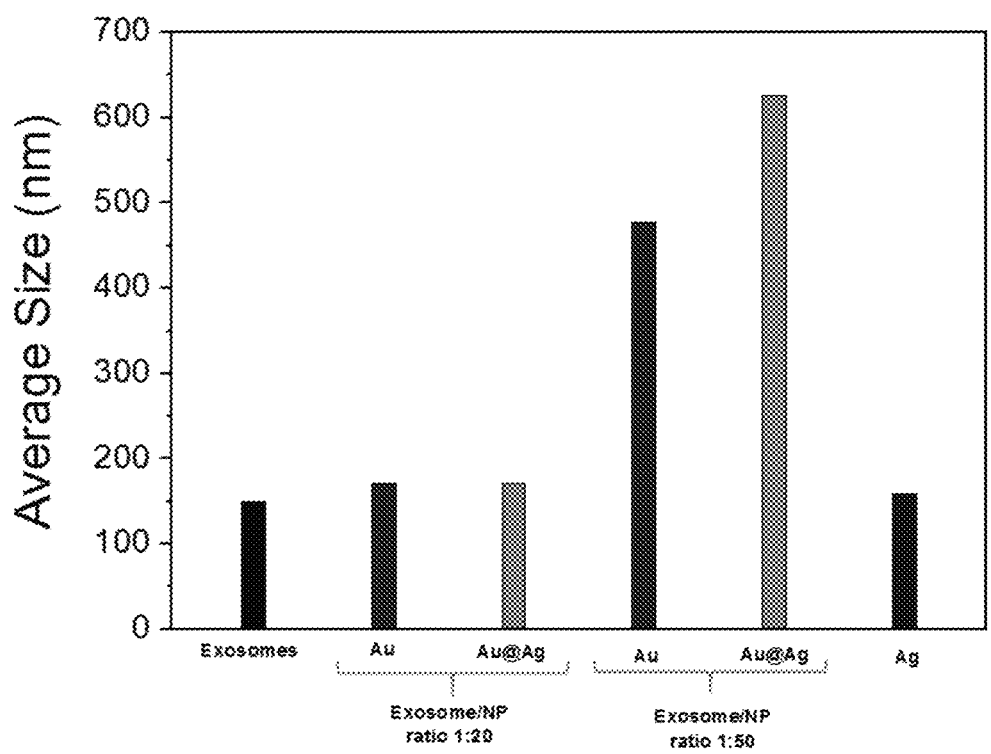
FIG. 28 shows the average size of the vesicles after addition of AuNP and Au@Ag NPs, illustrating features of embodiments of the present invention.

In addition, FIG. 28 shows in a comparatively way the stability of a colloidal dispersion for exosomes functionalized with Au NPs before and after the generation of the Ag layer. These results indicate that the synthesis could be performed without affecting the integrity of the exosomes. Two different ratios of Exosomes to nanoparticles. Results also are shown for Ag nanoparticles in the absence of gold nanoparticles.

With respect to the optical properties of the Au@Ag NPs, the EFEF is increased at least 1 order of magnitude for the case of Au@Ag NPs with respect to the Au NPs 20% cover. The difference in the EFEF could be explained considering that in the near field distribution for Ag@Au clusters, in spite of being irradiating at the same wavelength, different oscillating multipole modes of the clusters are being excited and that the molecules in this case are directly in contact with the metal surface (FIGS. 26A and 26B). It is important to note that the calculations of the variation of the EFEF was performed at a constant wavelength ($\lambda=785$ nm), and that these values of EFEF and eventually the trends would be different depending on the excitation wavelength.

The invention claimed is:

1. A method for characterizing extracellular vesicles at an individual level, the method comprising
    obtaining a sample comprising extracellular vesicles to be characterized,
    functionalizing the extracellular vesicles with plasmonic material by providing a coating of plasmonic material on the extracellular vesicles or applying at least one of plasmonic nanoparticles to the membrane, in a phospholipid layer or in the lumen of the extracellular vesicles,
    irradiating the functionalized individual extracellular vesicles with a laser beam and detecting a surface enhanced Raman spectroscopy signal from said functionalized individual extracellular vesicles, and
    identifying individual extracellular vesicles of the sample from the surface enhanced Raman spectroscopy signal.

2. A method according to claim 1, wherein the plasmonic material are plasmonic nanoparticles.

3. A method according to claim 1, wherein the functionalized individual extracellular vesicles are functionalized such that they are physico-chemically repelling each other.

4. A method according to claim 3, wherein the functionalized individual extracellular vesicles are functionalized such that they are separated from each other based on charge based repelling or based on steric effects.

5. A method according to claim 1, wherein the functionalized extracellular vesicles are colloidal stable in suspension.

6. A method according to claim 1, wherein the plasmonic material is functionalized with a positively charged small molecule and/or wherein the plasmonic material is functionalized using lipophilic or amphiphilic molecules for insertion into the phospholipid bilayer of the extracellular vesicles and/or wherein the plasmonic material is functionalized using particular targeting ligands for targeting extracellular vesicles.

7. A method according to claim 1, wherein the functionalized extracellular vesicles are, prior to performing said surface enhanced Raman scattering measurements, absorbed to a substrate so as to immobilize them and wherein for performing said surface enhanced Raman scattering measurements, the irradiation beam is scanned over the substrate for individually irradiating the coated extracellular vesicles.

8. A method according to claim 1, wherein the functionalized extracellular vesicles are in suspension, during said performing said surface enhanced Raman scattering measurements, wherein said surface enhanced Raman scattering measurements are performed on individual extracellular vesicles when these diffuse through the irradiation beam or are trapped.

9. A method according to claim 1, wherein the plasmonic material are metal based nanoparticles such as silver or titanium particles or wherein the plasmonic particles are carbon-based particles such as graphene particles, graphene oxide particles like graphene oxide nanosheets, carbon nanotubes, carbon nanodots, or fullerenes.

10. A method according to claim 1, wherein the plasmonic particles have a diameter within the range 1 to 100 nm.

11. A method according to claim 1, wherein the extracellular vesicles are exosomes.

12. A method according to claim 1, wherein after said detecting a surface enhanced Raman spectroscopy signal from said individual extracellular vesicle, the method comprises comparing said surface enhanced Raman spectroscopy signal with a library of surface enhanced Raman spectroscopy signals for identifying the individual extracellular vesicle.

13. A method according to claim 1, wherein functionalizing the extracellular vesicles with plasmonic material comprises binding gold nanoparticles to the surface of the extracellular vesicle and providing a plasmonic metal coating on the gold nanoparticles.

14. A method according to claim 13, wherein the gold nanoparticles are coated with a Ag metal layer the Ag metal coating having a thickness in the range 0.5-100 nm.

15. A microfluidic chip for characterization of extracellular vesicles, the microfluidic chip comprising
- an inlet for obtaining a sample comprising said extracellular vesicles to be characterized,
- plasmonic material contactable with said sample for forming a shell of plasmonic material around and/or for or applying at least one of plasmonic nanoparticles to the membrane, in a phospholipid layer or in the lumen of the extracellular vesicles,
- a microfluidic channel for guiding the functionalized extracellular vesicles to an irradiation position in the microfluidic chip, and
- the microfluidic chip being adapted for allowing laser radiation in the microfluidic chip at said irradiation position.

* * * * *